US010194793B2

(12) United States Patent
Du et al.

(10) Patent No.: US 10,194,793 B2
(45) Date of Patent: Feb. 5, 2019

(54) IMAGING FOR LOCAL SCALING

(71) Applicant: BEIJING ZHIGU RUI TUO TECH CO., LTD., Beijing (CN)

(72) Inventors: Lin Du, Beijing (CN); Wei Shi, Beijing (CN); Kuifei Yu, Beijing (CN)

(73) Assignee: Beijing Zhigu Rui Tuo Tech Co., Ltd., Beijing (CN)

( * ) Notice: Subject to any disclaimer, the term of this patent is extended or adjusted under 35 U.S.C. 154(b) by 201 days.

(21) Appl. No.: 14/905,262

(22) PCT Filed: Jul. 2, 2014

(86) PCT No.: PCT/CN2014/081492
§ 371 (c)(1),
(2) Date: Jan. 14, 2016

(87) PCT Pub. No.: WO2015/043275
PCT Pub. Date: Apr. 2, 2015

(65) Prior Publication Data
US 2016/0150951 A1    Jun. 2, 2016

(30) Foreign Application Priority Data

Sep. 30, 2013  (CN) .......................... 2013 1 0461019

(51) Int. Cl.
*G06K 9/32*         (2006.01)
*A61B 3/00*         (2006.01)
(Continued)

(52) U.S. Cl.
CPC ............ *A61B 3/0025* (2013.01); *A61B 3/103* (2013.01); *A61B 3/113* (2013.01); *A61B 3/12* (2013.01);
(Continued)

(58) Field of Classification Search
CPC ........... A61B 3/12; A61B 3/14; A61B 3/0025; A61B 3/113; G02B 2027/0185;
(Continued)

(56) References Cited

U.S. PATENT DOCUMENTS 5,839,000 A  * 11/1998  Davis, Jr. ............... G02B 7/102
                                                    396/51
6,965,394 B2 * 11/2005  Gutta ..................... H04N 5/232
                                                    348/14.05
(Continued)

FOREIGN PATENT DOCUMENTS

CH     102445756 A    5/2012
CH     102461177 A    5/2012
(Continued)

OTHER PUBLICATIONS

PCT International Search Report and Written Opinion dated Sep. 5, 2014, issued in corresponding International Application No. PCT/CN2014/081492 (8 pages).
(Continued)

*Primary Examiner* — Phuoc Tran
(74) *Attorney, Agent, or Firm* — Sheppard Mullin Richter & Hampton LLP

(57) ABSTRACT

An imaging method and device are provided for local scaling. The method can comprise determining a gazed object of an eye, determining the corresponding sub-areas of an imaging lens group according to the gazed object, the imaging lens group being configured to scale and image for the gazed object, comprising a plurality of sub-areas with adjustable scaling property, and determining the scaling parameter of the corresponding sub-areas according to the gazed object. In the method and the device of at least one embodiment of this application, the images of the gazed object in the user's fundus can be scaled in a local scaling mode, so as to avoid changing the overall view of the user
(Continued)

and to enable the user to conveniently observe the gazed object and to simultaneously correctly perceive the surrounding environment.

26 Claims, 16 Drawing Sheets

(51) Int. Cl.
    *H04N 5/232*     (2006.01)
    *G02B 7/36*     (2006.01)
    *G02B 27/01*     (2006.01)
    *A61B 3/103*     (2006.01)
    *A61B 3/113*     (2006.01)
    *A61B 3/12*     (2006.01)
    *A61B 3/14*     (2006.01)
    *G02C 7/08*     (2006.01)
    *G02C 11/00*     (2006.01)

(52) U.S. Cl.
    CPC ................. *A61B 3/14* (2013.01); *G02B 7/36* (2013.01); *G02B 27/0189* (2013.01); *G02C 7/081* (2013.01); *G02C 11/10* (2013.01); *H04N 5/232* (2013.01); *G02B 2027/0185* (2013.01); *G02B 2027/0187* (2013.01)

(58) Field of Classification Search
    CPC ........ G02B 2027/0187; G02B 27/0189; G02B 7/36; G02C 7/081; H04N 5/232
    See application file for complete search history.

(56) References Cited

U.S. PATENT DOCUMENTS

2006/0250322 A1    11/2006  Hall et al.
2012/0319928 A1*  12/2012  Rhodes ................ G02B 27/017
                                  345/8

FOREIGN PATENT DOCUMENTS

| CN | 101247461 A | 8/2008 |
| CN | 101448098 A | 6/2009 |
| CN | 103595912 A | 2/2014 |
| EP | 1403680 A1 | 3/2004 |
| JP | 2009251067 A | 10/2009 |
| WO | 2012/177378 A2 | 12/2012 |
| WO | WO 2012/165203 A1 | 12/2012 |

OTHER PUBLICATIONS

Office Action for Chinese Patent Application No. 201310461019.1 dated Apr. 28, 2016, with English Translation, 11 pages.

\* cited by examiner

IMAGING FOR LOCAL SCALING

CROSS-REFERENCE TO RELATED APPLICATION

This application is a national stage application of International Application No. PCT/CN2014/081492, filed on Jul. 2, 2014, which claims priority to and benefits of Chinese Patent Application No. 201310461019.1, entitled "Imaging Method and Device for Local Scaling", filed on Sep. 30, 2013. The contents of both of the above-referenced applications are incorporated herein by reference in their entirety.

TECHNICAL FIELD

This application relates to the technical field of imaging, and, more particularly, to imaging for local scaling.

BACKGROUND

For users with healthy eyes, when the objects viewed are smaller or farther, it is difficult for the eyes to observe desired details. For example, when persons sit in farther positions to view a ball game, it is difficult to view the details of limb movement and expressions of athletes. For users whose eyes per se have shortsightedness or farsightedness, when the objects viewed are smaller or farther, it is more difficult for the eyes to identify the details of the objects or persons viewed. Conversely, when the objects viewed are too large or too close, it is difficult for the users to observe the global information of the gazed at objects. For example, when the users stand in front of a high building or a mountain, it is difficult to observe the overall situation of the high building or the mountain.

Conventional optical scaling devices, such as a telescope or a magnifier usually adopt global unified scaling. FIG. 1a is a schematic diagram of the view of a user, wherein A, B, C represent three objects in the view 110. Assuming that the user wants to amplify the viewing object B, as shown in FIG. 1b, when a global unified scaling mode is adopted, the object B is amplified and meanwhile, the object C is also amplified, while the object A is out of the view 110, that is, at this moment, the user cannot see the object A. Thus, global unified scaling will cause a change in the integral view of the user. In many scenes, such as AR (Augmented Reality) environment, they will bring discomfort to the user, causing inconvenience for use.

SUMMARY

The following presents a simplified summary in order to provide a basic understanding of some example embodiments disclosed herein. This summary is not an extensive overview. It is intended to neither identify key or critical elements nor delineate the scope of the example embodiments disclosed. Its sole purpose is to present some concepts in a simplified form as a prelude to the more detailed description that is presented later.

At least one embodiment in this application aims at: providing an imaging device and method for local scaling so as to facilitate the user to view the gazing object.

According to one example embodiment of this application, a method comprises:

determining, by a system comprising a processor, a gazed object at which an eye is gazing;

determining corresponding sub-areas of an imaging lens group according to the gazed object, the imaging lens group being configured to scale and image for the gazed object, comprises a plurality of sub-areas with adjustable scaling property; and determining a scaling parameter of the corresponding sub-areas according to the gazed object.

According to another example embodiment of this application, an imaging device comprises:

an object determining unit configured to determine a gazed object of an eye;

an imaging lens group configured to scale and image for the gazed object, comprising a plurality of sub-areas with an adjustable scaling property;

a sub-area determining unit configured to determine corresponding sub-areas of the imaging lens group according to the gazed object; and a parameter determining unit configured to determine a scaling parameter of the corresponding sub-areas according to the gazed object.

According to another example embodiment of this application, a computer readable storage device, comprising at least one executable instruction, which, in response to execution, causes an imaging device comprising a processor to perform operations, comprising:

determining a gazed object of an eye;

determining corresponding sub-areas of an imaging lens group according to the gazed object; and determining a scaling parameter of the corresponding sub-areas according to the gazed object.

According to another example embodiment of this application, an imaging device, characterized by comprising a processor and a memory, the memory storing the executable instructions, the processor being connected with the memory through a communication bus, wherein, when the imaging device is operating, the processor executes or facilitates execution of the executable instructions stored by the memory to cause the imaging device to perform operations, comprising:

determining a gazed object of an eye;

determining corresponding sub-areas of an imaging lens group according to the gazed object; and determining a scaling parameter of the corresponding sub-areas according to the gazed object.

In the method and the device of at least one embodiment in this example embodiment, adopts the imaging lens group comprising a plurality of sub-areas with adjustable scaling property to scale and image for the gazing object of the eye and can automatically determine the scaling parameter of the corresponding sub-areas according to the gazing object, thus scaling the images of the gazing object on the user's fundus by locally scaling, avoiding changing the whole view of the user, facilitating the user's observation for the gazing object and also enabling the user to correctly perceive the surrounding environment.

DETAILED DESCRIPTION

The concrete implementations of this application are further described in details in combination with the drawings and the embodiments. The following embodiments are used for illustrating this application, but do not limit the range of this application.

Figure 1A:
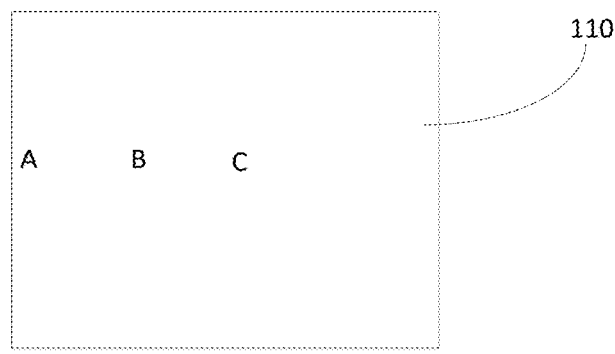
FIG. 1a is an example schematic diagram of the view of a user.
Figure 1B:
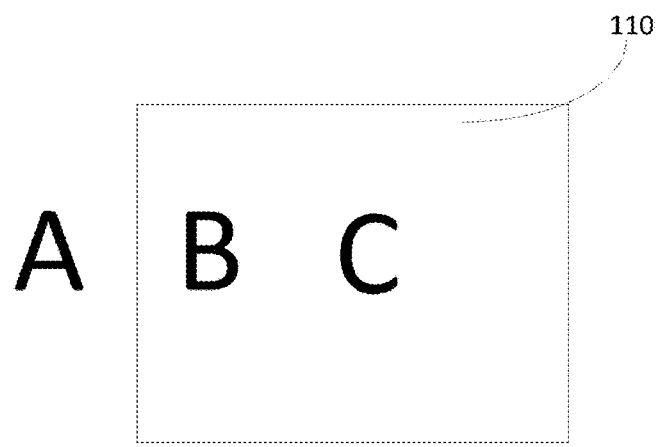
FIG. 1b is an example schematic diagram after objects in the view of the user are uniformly scaled.
Figure 1C:
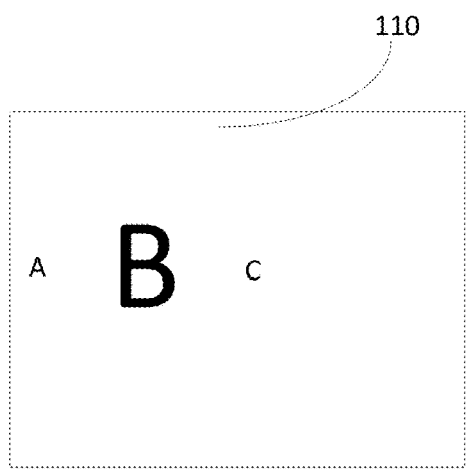
FIG. 1c is an example schematic diagram after objects in the view of the user are locally scaled.

In many application scenes, the user only hopes to locally scale the viewed object and keep a feeling of distance from the surrounding environment. For example, when the user is driving, the user hopes to carefully observe the license plate numbers of front distant vehicles while does not hope to neglect other vehicles on the road (if other vehicles are neglected, danger may occur). At this time, the unified scaling mode should not be used for changing the overall view of the user. Thus, at least one embodiment of this application provides an imaging method for local scaling. When the method of this embodiment is adopted for amplifying the object B in the user's view shown in FIG. 1a, its effect is shown in FIG. 1c. It can be seen that in the amplified view, only the object B is amplified, while the object A and the object C keep the original objects. Moreover, the integral size of the user's view is not changed, and the object A is still within the view 110.

Figure 2:
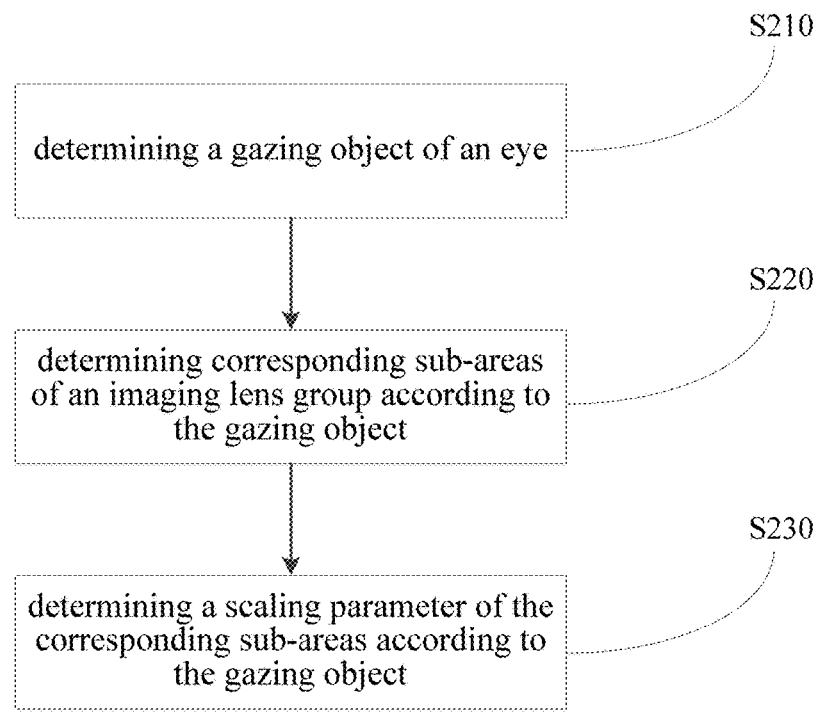
FIG. 2 is an example flow diagram of the imaging method for local scaling in an embodiment of this application.

As shown in FIG. 2, the method comprises:

S210: determining the gazing object of an eye.

Wherein, the gazing object generally means an object, a person, etc. viewed by the user with the observing time more than predetermined time, and may be a static object or a mobile object.

S220: determining the corresponding sub-areas of an imaging lens group according to the gazing object.

Wherein, the imaging lens group is configured to scale and image for the gazing object, comprising a plurality of sub-areas with adjustable scaling property.

S230: determining the scaling parameter of the corresponding sub-areas according to the gazing object; and adjusting the scaling property of the corresponding sub-areas according to the scaling parameter after determining the scaling parameter.

In the method of this embodiment, adopts the imaging lens group comprising a plurality of sub-areas with adjustable scaling property to scale and image for the gazing object of the eye and can automatically determine the scaling parameter of the corresponding sub-areas according to the gazing object, thus scaling the images of the gazing object on the user's fundus by locally scaling, preventing the whole view of the user from being changed, and facilitating the user's observation for the gazing object.

Specifically, the step S210 can adopt any one of the following several realization ways:

1) detecting the position of the focus point of the eye, and determining the gazing object according to the position of the focus point of the eye.

Wherein, the detection of the position of the focus point of the eye may have several realization ways, and three optional realization ways are provided as follows:

a) determining the position of the focus point of the eye according to an optical parameter corresponding to images presented on the fundus and with the clarity greater than a preset value; and the optical parameter being the optical parameter of an optical path between an image collection position and the eye.

Specifically, the realization way a) comprises:

S111: collecting fundus images.

S112: adjusting the imaging parameter of the optical path between the eye and the image collection position for collecting images with the clarity greater than the preset value.

S113: processing the collected images; acquiring the optical parameter of the eye according to an imaging parameter corresponding to the images with the clarity greater than the preset value; and the imaging parameter being the imaging parameter of the optical path between the image collection position and the eye. The step S113 specifically comprises: analyzing the collected images to find out the images with the clarity greater than the preset value; and calculating the optical parameter of the eye according to the images with the clarity greater than the preset value and the imaging parameter of the optical path corresponding to the images with the clarity greater than the defined value.

Wherein, in the step S113, in order to improve the accuracy, the collected images may be analyzed to select out the clearest image from the images with the clarity greater than the preset value, and the optical parameter of the eye is calculated according to the clearest image and the imaging parameter of the optical path corresponding to the clearest image.

S114: calculating the position of the focus point of the eye according to the optical parameter of the eye. Wherein, the optical parameter of the eye comprises: equivalent focal length and line-of-sight direction of the eye.

b) tracking the line-of-sight directions of two eyes and acquiring the position of the focus point of the eye through the intersection of the line-of-sight directions of the two eyes.

c) tracking the line-of-sight directions of the eye; acquiring the scene depth of the position of the focus point containing the eye according to the line-of-sight directions; and calculating and acquiring the position of the focus point of the eye according to the scene depth.

2) collecting fundus images and determining the gazing object according to the fundus images.

There is a macular area in the center of the retina of human fundus, and the macular area, located in the central optical zone of human eye, is a projection point of the eye light axis. A depression in the center of the yellow spot, known as a central fovea, is the sharpest part of an eye, and the eye's gazing object is projected to the central fovea of the macular area. Accordingly, the user's gazing object may be determined by collecting the corresponding images at the central fovea of the macular area in the fundus images.

When corresponding sub-areas of the imaging lens group are determined in the step S120, the corresponding sub-areas may be determined according to the projection of the gazing object on the imaging lens group.

Wherein, the imaging lens group comprises at least two lenses, and the at least two lenses being adjustable in scaling property with each corresponding portion of the sub-areas. The scaling property may be adjusted by changing the respective focal lengths of the at least two lenses or by changing the relative position between the at least two lenses. In the imaging lens group, the sub-areas are distributed in an array, such as in a rectangular array, or distributed in a radial concentric circle array.

The projection of the gazing object on the imaging lens group along the line-of-sight directions covers some relevant sub-areas, i.e., the corresponding sub-areas, and these corresponding sub-areas covered by the projection are the sub-areas required to be adjusted in the scaling property.

After the sub-areas required to be adjusted in the scaling property are determined, the corresponding scaling parameter is required to be determined. The step S130 may use any one of the following several implementations:

1) The scaling parameter of the corresponding sub-areas is determined according to the actual viewing distance from the gazing object to the eye. Specifically, this manner 1) may also comprise:

Mode d:

acquiring the actual viewing distance from the gazing object to the eye; and determining the scaling parameter of the corresponding sub-areas according to the actual viewing distance. Alternatively, Mode e:

presetting the target viewing distance from the gazing object to the eye and the buffer of the target viewing distance;

acquiring the actual viewing distance from the gazing object to the eye; and determining the scaling parameter of the corresponding sub-areas according to the target viewing distance, the actual viewing distance and the buffer.

Wherein, in the modes d and e, acquiring the actual viewing distance from the gazing object to the eye may be realized according to the equivalent focal length of the eye in above mode a or by calculating the same after the position of the focus point of the eye is acquired according to the above modes b and c.

In mode d, the scaling parameter of the corresponding sub-areas determined according to the actual viewing distance may be a magnification, and there are various modes for acquiring the magnification according to the actual viewing distance; for example, the corresponding magnification is determined according to a piecewise function corresponding to the viewing distance or by looking up the table. This implementation selects a quick way of looking up table, i.e., presetting a corresponding relation table between the actual viewing distance and the magnification, and then determining the currently needed magnification by looking up the table during the implementation of the method. Wherein, the magnification may be 1, a constant greater than 1, or a grade greater than zero and smaller than 1. Table 1 below is an example of a magnification list, and it is observed that corresponding to each actual viewing distance $D_O$, a preset magnification $T_2$ is stored in Table 1; for example, when the actual viewing distance $D_0$ is 20 m, its corresponding magnification may be determined as 5 by looking up the table.

TABLE 1

First Magnification List

| Actual Viewing Distance $D_O$ (in m) | Magnification $T_2$ |
|---|---|
| $D_O > 100$ | 10 |
| $10 < D_O \leq 100$ | 5 |
| $1 < D_O \leq 10$ | 2 |
| $0.3 < D_O \leq 1$ | 1 |

TABLE 1-continued

First Magnification List

| Actual Viewing Distance $D_O$ (in m) | Magnification $T_2$ |
|---|---|
| $0.1 < D_O \leq 0.3$ | $2/3$ |
| $0 < D_O \leq 0.1$ | $1/2$ |

In mode e, the target viewing distance is the viewing distance of user's eye expected to reach, i.e., the desired value of the viewing distance when the user observes the gazing object, such as 10 m. When the user's eye's actual viewing distance is the target viewing distance, the user will feel that the distance from the gazing object to the himself or herself is moderate and the fundus images will be not too large or too small. Besides, the target viewing distance that makes the user feel comfortable is generally not a distance point, but rather a distance range; accordingly, the buffer of the target viewing distance is also arranged in the mode e. Generally, the buffer of the target viewing distance is the distance range preset between both sides of the target viewing distance. For example, assuming that the target viewing distance is $D_T$, the buffer may be (($D_T-D_L$, $D_T$)∪($D_T$, $D_T+D_R$)), wherein, $D_T$, $D_L$ and $D_R$ are constants. Consequently, the viewing distance scope ($D_T-D_L$, $D_T+D_R$) is set to the viewing distance scope that makes the user feel comfortable. $D_L$ may be equal to $D_R$; in this case, the first sub-buffer (($D_T-D_L$, $D_T$) and the second sub-buffer ($D_T$, $D_T+D_R$) of the buffer of the target viewing distance are of equal size and take $D_T$ as the center; and $D_L$ may also be unequal to $D_R$; in this case, the first sub-buffer (($D_T-D_L$, $D_T$) and the second sub-buffer ($D_T$, $D_T+D_R$) vary in size.

In the step of determining the scaling parameter of the corresponding sub-areas according to the target viewing distance, the actual viewing distance and the buffer, for the scaling parameter:

Under the circumstance that the actual viewing distance is less than the target viewing distance and the actual viewing distance is beyond the buffer of the target viewing distance, after the scaling property of the corresponding sub-areas is adjusted according to the scaling parameter, the actual viewing distance will be increased to the target viewing distance, to shrink the fundus images of the gazing object.

Under the circumstance that the actual viewing distance is greater than the target viewing distance and the actual viewing distance is beyond the buffer of the target viewing distance, after the scaling property of the corresponding sub-areas is adjusted according to the scaling parameter, the actual viewing distance will be decreased to the target viewing distance, to amplify the fundus images of the gazing object.

In some implementations demanding simple control, the buffer of the target viewing distance may be set as zero, i.e., equivalent to the buffer without setting the target viewing distance; in this case, this is equivalent to determining the scaling parameter of the corresponding sub-areas according to the target viewing distance and the actual viewing distance, for the scaling parameter:

Under the circumstance that the actual viewing distance is less than the target viewing distance, after the scaling property of the corresponding sub-areas is adjusted according to the scaling parameter, the actual viewing distance will be increased to the target viewing distance, to shrink the fundus images of the gazing object.

Under the circumstance that the actual viewing distance is greater than the target viewing distance, the scaling property of the corresponding sub-areas is adjusted according to the scaling parameter, the actual viewing distance will be decreased to the target viewing distance, to amplify the fundus images of the gazing object.

2) determining the scaling parameter of the corresponding sub-areas according to the actual area proportion of the fundus images of the gazing object on the fundus. Specifically, this manner 2) may also comprise:

Mode f:

acquiring the actual area proportion of the fundus images of the gazing object on the fundus; and determining the scaling parameter of the corresponding sub-areas according to the actual area proportion. Alternatively, Mode g:

presetting the target area proportion of the fundus images of the gazing object on the fundus and the buffer of the target area proportion;

acquiring the actual area proportion of the fundus images of the gazing object on the fundus; and determining the scaling parameter of the corresponding sub-areas according to the target area proportion, the actual area proportion and the buffer.

Wherein, in modes d and e, the area of the user's fundus is generally fixed, after the user's fundus images are collected, the images in the central fovea area of the yellow spot may be extracted therefrom and used as the fundus images of the gazing object, such that the area of the fundus images of the gazing object may be acquired and then the actual area proportion of the fundus images of the gazing object on the fundus may be acquired.

In the mode f, the scaling parameter of the corresponding sub-areas determined according to the actual area proportion may be a magnification, and there are various modes for determining the corresponding magnification according to the actual area proportion, for example, the corresponding magnification is determined according to the piecewise function corresponding to the actual area proportion or by looking up the table. This implementation selects a quick way of looking up table, i.e., presetting a corresponding relation table between the actual area proportion and the magnification, and then determining the currently needed magnification by looking up the table during the implementation of the method. Wherein, the magnification may be 1, a constant greater than 1, or a grade greater than zero and smaller than 1. Table 2 below is an example of a magnification list, and it is observed that corresponding to each actual area proportion $S_{RE}$, a preset magnification $T_1$ is stored in Table 2; for example, when the actual area proportion $S_{RE}$ is 20%, its corresponding magnification may be determined as 2 by looking up the table.

TABLE 2

Second Magnification List

| Actual Area Proportion $S_{RE}$ | Magnification $T_1$ |
|---|---|
| $0 < S_{RE} \leq 5\%$ | 15 |
| $5\% < S_{RE} \leq 10\%$ | 6 |
| $10\% < S_{RE} \leq 30\%$ | 2 |
| $30\% < S_{RE} \leq 70\%$ | 1 |
| $70\% < S_{RE} \leq 90\%$ | $2/3$ |
| $90\% < S_{RE} \leq 100\%$ | $1/2$ |

In the mode g, the target area proportion is the area proportion of the fundus images of the gazing object on the fundus expected to achieve, such as 50%. Under the circumstance that the area proportion of the fundus images of the gazing object on the fundus is the target area proportion, the user will feel that the distance from the gazing object to himself or herself is moderate and the fundus images will be not too large or too small. Besides, the area proportion of the fundus images of the gazing object that makes the user feel comfortable is generally not an area proportion point, but rather an area proportion range; accordingly, the buffer of the target area proportion is also arranged in the mode g. Generally, the buffer is the area proportion range preset between both sides of the target area proportion. For example, assuming that the target area proportion is $S_T$, the buffer may be $((S_T-S_L, S_T) \cup (S_T, S_T+S_R))$, wherein, and v are constants. Consequently, the region of area proportion $S_T-S_L, S_T+S_R)$ is set as the region of area proportion that makes the user feel comfortable. $S_L$ may be equal to $S_R$; in this case, the third sub-buffer $(S_T-S_L, S_T)$ and the fourth sub-buffer $(S_T, S_T+S_R)$ of the buffer are of equal size and take $S_T$ as the center; and $S_L$ may also be unequal to $S_R$; in this case, the third sub-buffer $(S_T-S_L, S_T)$ and the fourth sub-buffer $(S_T, S_T+S_R)$ vary in size.

In the step of determining the scaling parameter of the corresponding sub-areas according to the target area proportion, the actual area proportion and the buffer, for the scaling parameter:

In the case that the actual area proportion is less than the target area proportion and the actual area proportion is beyond the buffer, after the scaling property of the corresponding sub-areas is adjusted according to the scaling parameter, the fundus images of the gazing object may be amplified to the target area proportion.

In the case that the actual area proportion is greater than the target area proportion and the actual area proportion is beyond the buffer, after the scaling property of the corresponding sub-areas is adjusted according to the scaling parameter, the fundus images of the gazing object may be shrunk to the target area proportion.

In some implementations demanding simple control, the buffer may also be set as zero, i.e., equivalent to not setting the buffer; in this case, this is equivalent to determining the scaling parameter of the corresponding sub-areas according to the target area proportion and the actual area proportion, for the scaling parameter:

In the case that the actual area proportion is less than the target area proportion, after the scaling property of the corresponding sub-areas is adjusted according to the scaling parameter, the fundus images of the gazing object may be amplified to the target area proportion.

In the case that the actual area proportion is greater than the target area proportion, after the scaling property of the corresponding sub-areas is adjusted according to the scaling parameter, the fundus images of the gazing object may be shrunk to the target area proportion.

In order to avoid the condition that the user's fundus images are changed in ungazing state, such as random sweeping, to affect the user experience, the method may also comprise:

S240: judging whether the time for the eye to observe the gazing object exceeds the predetermined time or not, and if exceeded, executing the steps S220 and S230.

Wherein, the predetermined time shall be set in such a manner to just make sure that the user is gazing the current observation object, and generally, when human eyes view a target, an optical impression may be obtained with the minimum observation time of 0.07-0.3 s, and the predetermined time shall be more than the minimum observation time; for example, it may be set at 1 s, 2 s, etc. In addition, the time for the user to observe the gazing object may be acquired by monitoring the time when the position of the focus point of user's eye remains unchanged, and under the circumstance that the time when the position of the focus point of user's eye remains unchanged exceeds the predetermined time, it can be judged that the user is currently gazing the object in the position of the focus point, or acquired by monitoring the dwell time of the corresponding image in the central fovea of the yellow spot, and under the circumstance that the dwell time of the image corresponding to the same object in the central fovea exceeds the predetermined time, it can be judged that the user is currently gazing the object.

When the gazing object is a mobile object, the judgment is only made in the beginning on whether the time for the eye to observe the mobile object exceeds the predetermined time, once the time is judged to exceed the predetermined time, the steps S220 and S230 are triggered; and when the user's line-of-sight follows the mobile object, the judgment would not be made again on whether the gazing time exceeds the predetermined time as long as the user's eye are gazing the mobile object all the time (the user does not need to turn his or her head but move his or her eyeballs only), thereby facilitating the user in observing the scaling of the mobile object.

In addition, human eyes may have ametropia problems such as farsightedness, nearsightedness and/or astigmatism, and therefore, the method also comprises:

S250: judging whether the eye have ametropia problems and generating the ametropia information about the eye if the eye have ametropia problems;

correspondingly, in this case, the step S230 comprises:

determining the scaling parameter of the corresponding sub-areas according to the gazing object and the ametropia information.

It should be understood that, in various embodiments of the present invention, the sequence numbers of the above processes do not imply an execution sequence, and the execution sequence of the processes should be determined according to the functions and internal logic, which is not intended to limit the implementation processes of the embodiments of the present invention in any way.

From the above, the method of this embodiment can scale the images of the gazing object on the user's fundus in a local scaling mode, so as to avoid changing the overall view of the user and to facilitate the user's observation for the gazing object.

Furthermore, the embodiment of this application also provides a computer readable medium comprising computer readable instructions which implement the following operation when they are executed: the operation of executing the steps S210, S220 and S230 of the method in the above-mentioned implementation shown in FIG. 2.

Figure 3A:
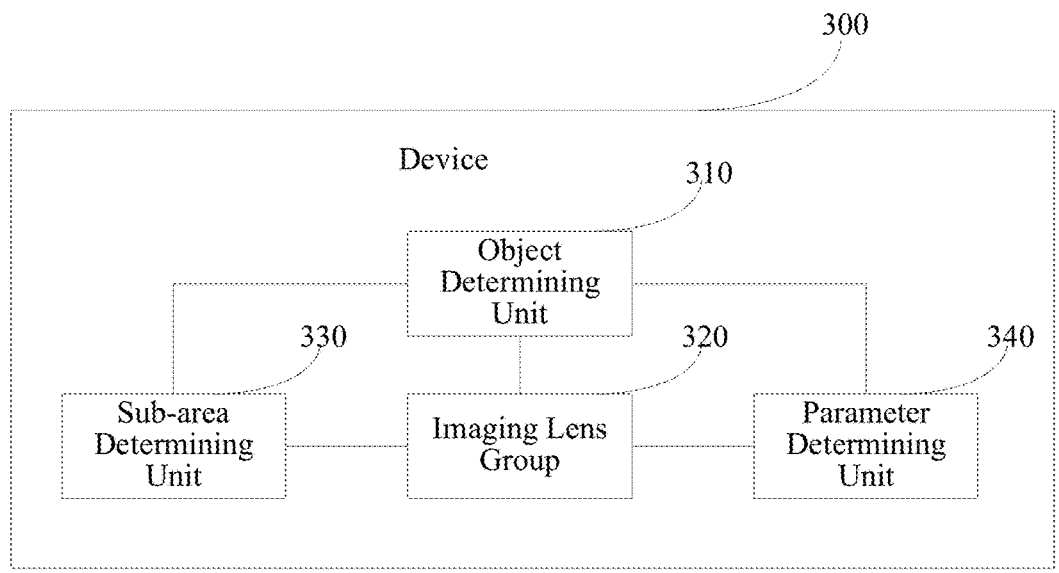
FIG. 3a is an example structural diagram of a module of an implementation of the imaging device for local scaling in an embodiment of this application.

The embodiment of this application also provides an imaging device for local scaling, as shown in FIG. 3a, the device 300 comprises: an object determining unit 310, an imaging lens group 320, a sub-area determining unit 330 and a parameter determining unit 340.

The object determining unit 310 is configured to determine the gazing object of the eye.

The imaging lens group 320 is configured to scale and image for the gazing object and comprises a plurality of sub-areas with adjustable scaling property.

The sub-area determining unit 330 is configured to determine the corresponding sub-areas of the imaging lens group according to the gazing object.

The parameter determining unit 340 is configured to determine the scaling parameter of the corresponding sub-areas according to the gazing object.

The device of this embodiment uses the imaging lens group comprising a plurality of sub-areas with adjustable scaling property to scale and image for the gazing object of the eye and can automatically determine the scaling parameter of the corresponding sub-areas according to the gazing object, thus scaling the images of the gazing object on the user's fundus in a local scaling mode, so as to avoid changing the overall view of the user and to facilitate the user's observation for the gazing object.

Figure 3B:
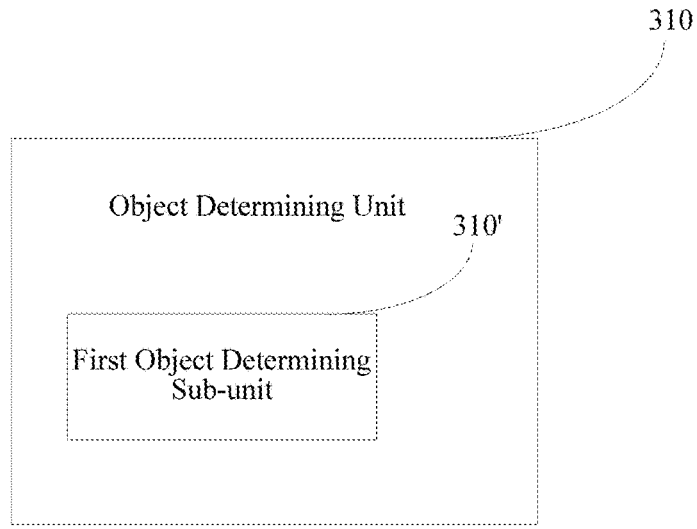
FIG. 3b is an example structural diagram of a module of the object determining unit in an embodiment of this application.

Specifically, the object determining unit 310 may use any one of the following several implementations:

1) As shown in FIG. 3b, the object determining unit 310 may comprise a first object determining sub-unit 310' configured to detect the position of the focus point of an eye and determining the gazing object according to the position of the focus point of the eye.

Figure 3C:
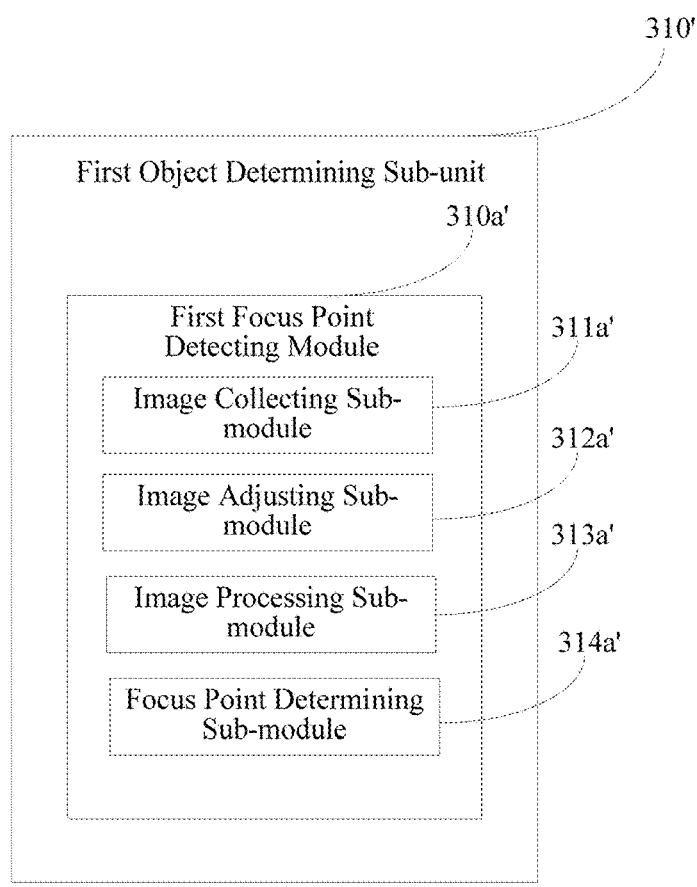
FIG. 3c is an example structural diagram of a module of the first object determining sub-unit in an embodiment of this application.

Wherein, the function of the first object determining sub-unit 310' may be realized in various modes and three optional implementations are provided as follows:

a) As shown in FIG. 3c, the first object determining sub-unit 310' may comprise a first focus point detecting module 310a' configured to determine the position of the focus point of the eye according to an optical parameter corresponding to the images presented on the fundus and with the clarity greater than a preset value, and the optical parameter being the optical parameter of the optical path between the image collection position and the eye.

Specifically, the first focus point detecting module 310a' comprises:

an image collecting sub-module 311a' configured to collect fundus images;

an image adjusting sub-module 312a' configured to adjust the imaging parameter of the optical path between the eye and the image collection position to collect the images with the clarity greater than the preset value; and an image processing sub-module 313a' configured to process the collect images and acquire the eye's optical parameter according to the imaging parameter corresponding to the images with the clarity greater than the preset value, and the imaging parameter being the imaging parameter of the optical path between the image collection position and the eye. The image processing sub-module is specifically configured to: analyze the collected images to find out the images with the clarity greater than the preset value; and calculate the optical parameter of the eye according to the images with the clarity greater than the preset value and the imaging parameter of the optical path corresponding to the images with the clarity greater than the preset value. Wherein, in order to improve the accuracy, the collected images may be analyzed to select out the clearest image from the images with the clarity greater than the preset value, and the optical parameter of the eye is calculated according to the clearest image and the imaging parameter of the optical path corresponding to the clearest image.

a focus point determining sub-module 314a' configured to calculate the position of the focus point of the eye according to the optical parameter of the eye. Wherein, the optical parameter of the eye comprises: equivalent focal length and line-of-sight directions of the eye.

Figure 3D:
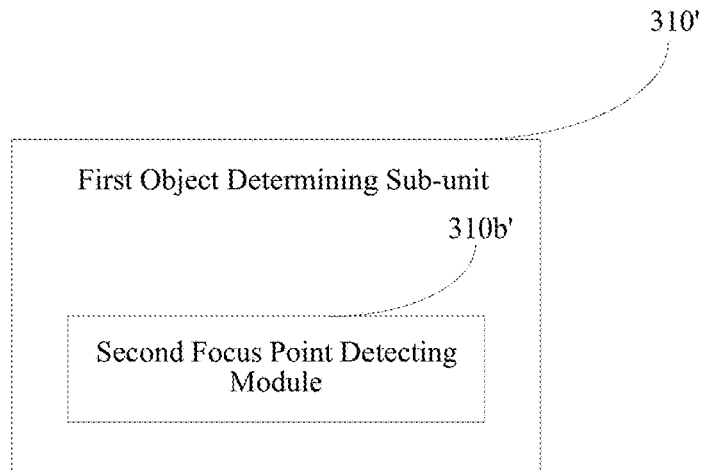
FIG. 3d is an example structural diagram of another module of the first object determining sub-unit in an embodiment of this application.
Figure 3E:
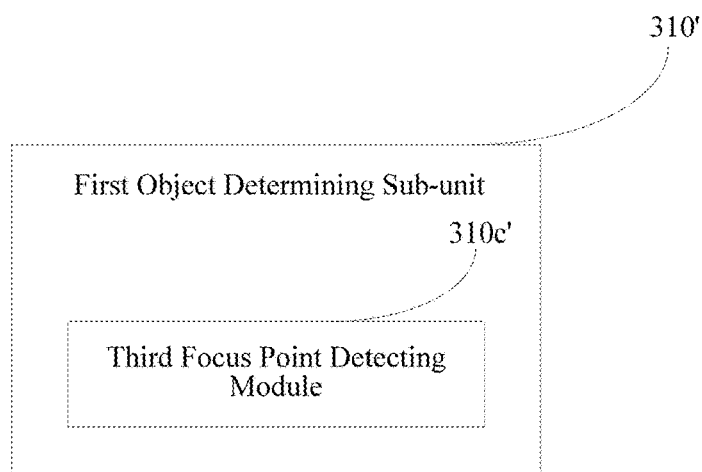
FIG. 3e is an example structural diagram of another module of the first object determining sub-unit in an embodiment of this application.

The function of the first focus point detecting module may be realized by using a focus point detecting system of the eye, the focus point detecting system of the eye will be detailed below, and the details are not described here.

b) As shown in FIG. 3d, the first object determining sub-unit 310' may comprise a second focus point detecting module 310b' configured to track the line-of-sight directions of two eyes to obtain the position of the focus point of the eye through the intersection of the line-of-sight directions of the two eyes.

c) As shown in FIG. 3e, the first object determining sub-unit 310' may comprise a third focus point detecting module 310c' configured to track the line-of-sight directions of the eye, obtain the scene depth of the position of the focus point containing the eye according to the line-of-sight directions, and calculate and obtain the position of the focus point of the eye according to the scene depth.

Figure 3F:
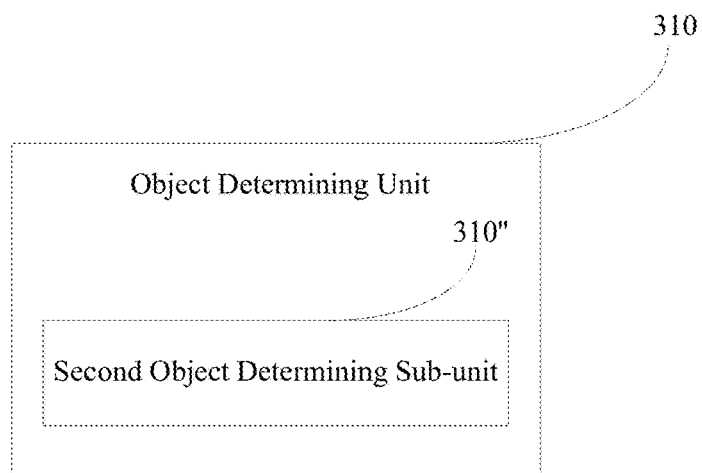
FIG. 3f is an example structural diagram of a module of the object determining unit in an embodiment of this application.

2) As shown in FIG. 3f, the object determining unit 310 may comprise a second object determining sub-unit 310" configured to collect the fundus images and determine the gazing object according to the fundus images.

There is a macular area in the center of the retina of human fundus, and the macular area, located in the central optical zone of human eyes, is a projection point of the eyes light axis. A depression in the center of the yellow spot, known as a central fovea, is the sharpest part of an eye, and the eye's gazing object is projected to the central fovea of the macular area. Accordingly, the user's gazing object may be determined by collecting the corresponding images at the central fovea of the macular area in the fundus images.

The imaging lens group 320 comprises at least two lenses, and the at least two lenses being adjustable in the scaling property with each corresponding portion of the sub-areas. The scaling property may be adjusted by changing the respective focal lengths of the at least two lenses or by changing the relative position between the at least two lenses. In the imaging lens group, the sub-areas are distributed in an array, such as in a rectangular array, or distributed in a radial concentric circle array.

When the corresponding sub-areas of the imaging lens group 320 are determined by the sub-area determining unit 330, the corresponding sub-areas may be determined according to the projection of the gazing object on the imaging lens group 320. The projection of the gazing object on the imaging lens group along the line-of-sight directions covers some relevant sub-areas, i.e., the corresponding sub-areas, and these corresponding sub-areas covered by the projection are the sub-areas required to be adjusted in the scaling property.

Figure 3G:
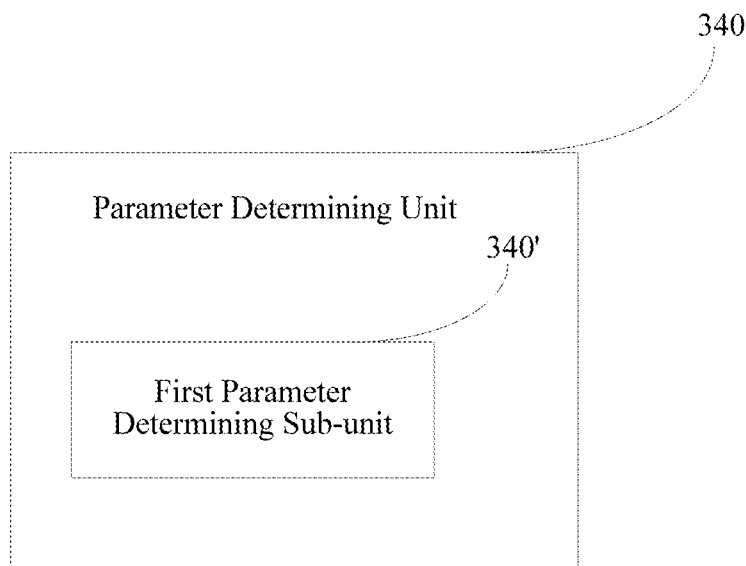
FIG. 3g is an example structural diagram of a module of the parameter determining unit in an embodiment of this application.

After the sub-areas required to be adjusted in the scaling property are determined, the corresponding scaling parameter is required to be determined. The parameter determining unit 340 may use any one of the following several implementations:

1) As shown in FIG. 3g, the parameter determining unit 340 may comprise a first parameter determining sub-unit 340' configured to determine the scaling parameter of the corresponding sub-areas according to the actual viewing distance from the gazing object to the eye.

Figure 3H:
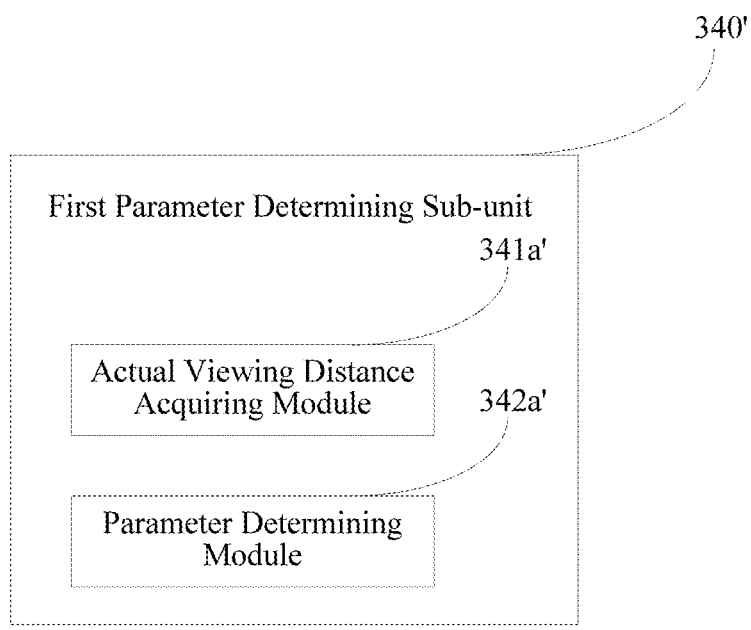
FIG. 3h is an example structural diagram of a module of the first parameter determining sub-unit in an embodiment of this application.

Specifically, as shown in FIG. 3h, in an optional implementation, the first parameter determining sub-unit 340' may comprise:

an actual viewing distance acquiring module 341a' configured to acquire the actual viewing distance from the gazing object to the eye. Wherein, acquiring the actual viewing distance from the gazing object to the eye may be realized according to the equivalent focal length of the eye acquired by the first focus point detecting module or by calculating the same according to the position of the focus point of the eye acquired by the second focus point detecting module or the third focus point detecting module.

a parameter determining module 342a' configured to determine the scaling parameter of the corresponding sub-areas according to the actual viewing distance. Wherein, the scaling parameter of the corresponding sub-areas determined according to the actual viewing distance may be a magnification, and there are various modes configured to acquire the magnification according to the actual viewing distance; for example, the corresponding magnification is determined according to a piecewise function corresponding to the viewing distance or by looking up the table. This implementation selects a quick way of looking up table, i.e., presetting a corresponding relation table between the actual viewing distance and the magnification, and then determining the currently needed magnification by looking up the table during the implementation of the method. The corresponding relation table between the actual viewing distance and the magnification is shown in Table 1, and the details are not described here.

Figure 3I:
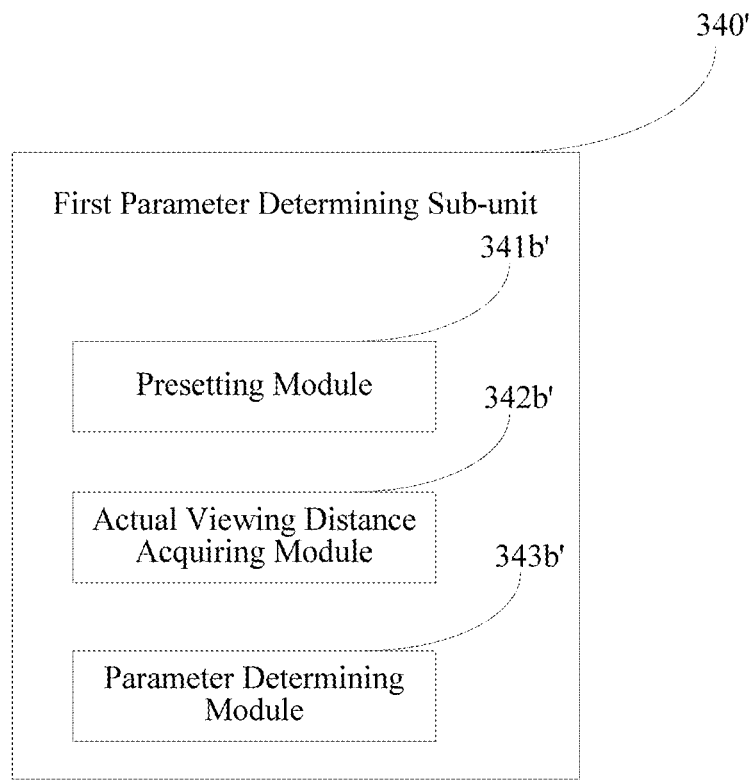
FIG. 3i is an example structural diagram of another module of the first parameter determining sub-unit in an embodiment of this application.

In another optional implementation, as shown in FIG. 3i, the first parameter determining sub-unit 340' comprises:

a presetting module 341b' configured to preset the target viewing distance from the gazing object to the eye and the buffer of the target viewing distance. Wherein, the target viewing distance is the viewing distance of user's eye expected to reach, i.e., the desired value of the viewing distance when the user observes the gazing object, such as 10 m. When the user's eye's actual viewing distance is the target viewing distance, the user will feel that the distance from the gazing object to himself or herself is moderate and the fundus images will be not too large or too small. Besides, the target viewing distance that makes the user feel comfortable is generally not a distance point, but rather a distance range; accordingly, the buffer of the target viewing distance is also arranged in the mode e. Generally, the buffer of the target viewing distance is the distance range preset between both sides of the target viewing distance. For example, assuming that the target area proportion is $D_T$, the buffer may be $((D_T-D_L, D_T) \cup (D_T, D_T+D_R))$, wherein, $D_T$, $D_L$ and $D_R$ are constants. Consequently, the scope of viewing distance $(D_T-D_L, D_T+D_R)$ is set as the scope of viewing distance that makes the user feel comfortable. $D_L$ may be equal to $D_R$; in this case, the first sub-buffer $((D_T-D_L, D_T)$ and the second sub-buffer $(D_T, D_1+D_R)$ of the buffer of the target viewing distance are of equal size and take $D_T$ as the center; and $D_L$ may also be unequal to $D_R$; in this case, the first sub-buffer $((D_T-D_L, D_T)$ and the second sub-buffer $(D_T, D_T+D_R)$ vary in size.

an actual viewing distance acquiring module 342b' configured to acquire the actual viewing distance from the gazing object to the eye. The actual viewing distance acquiring module may be the same as that in the above implementation, and the details are not described here again.

a parameter determining module 343b' configured to determine the scaling parameter of the corresponding sub-areas according to the target viewing distance, the actual viewing distance and the buffer.

Wherein, in the step of determining the scaling parameter of the corresponding sub-areas according to the target viewing distance, the actual viewing distance and the buffer, for the scaling parameter:

Under the circumstance that the actual viewing distance is less than the target viewing distance and the actual viewing distance is beyond the buffer of the target viewing distance, after the scaling property of the corresponding sub-areas is adjusted according to the scaling parameter, the actual viewing distance will be increased to the target viewing distance, to shrink the fundus images of the gazing object.

Under the circumstance that the actual viewing distance is greater than the target viewing distance and the actual viewing distance is beyond the buffer of the target viewing distance, after the scaling property of the corresponding sub-areas is adjusted according to the scaling parameter, the actual viewing distance will be decreased to the target viewing distance, to amplify the fundus images of the gazing object.

In some implementations demanding simple control, the buffer of the target viewing distance may be set as zero, i.e., equivalent to the buffer without setting the target viewing distance; in this case, this is equivalent to determining the scaling parameter of the corresponding sub-areas according to the target viewing distance and the actual viewing distance, for the scaling parameter:

Under the circumstance that the actual viewing distance is less than the target viewing distance, after the scaling property of the corresponding sub-areas is adjusted according to the scaling parameter, the actual viewing distance will be increased to the target viewing distance, to amplify the fundus images of the gazing object.

Under the circumstance that the actual viewing distance is greater than the target viewing distance, after the scaling property of the corresponding sub-areas is adjusted according to the scaling parameter, the actual viewing distance will be decreased to the target viewing distance, to amplify the fundus images of the gazing object.

Figure 3J:
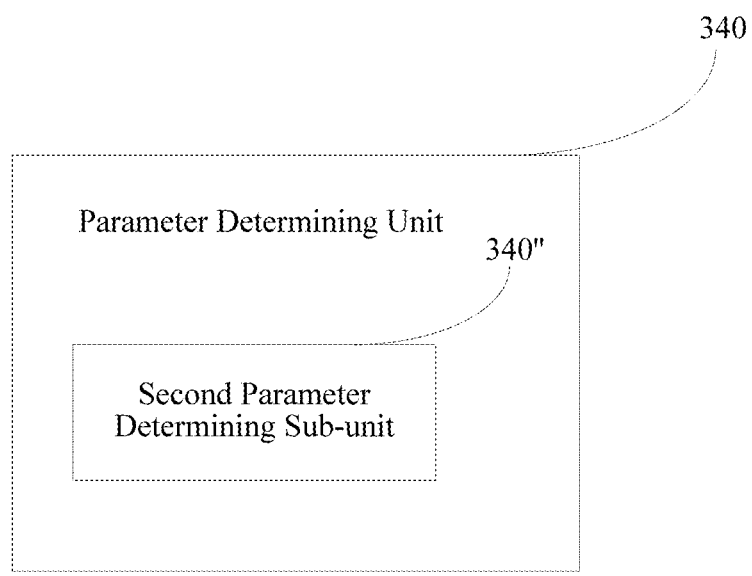
FIG. 3j is an example structural diagram of a module of the parameter determining unit in an embodiment of this application.

2) As shown in FIG. 3j, the parameter determining unit 340 may comprise a second parameter determining sub-unit 340" configured to determine the scaling parameter of the corresponding sub-areas according to the actual area proportion of the fundus images of the gazing object on the fundus.

Figure 3K:
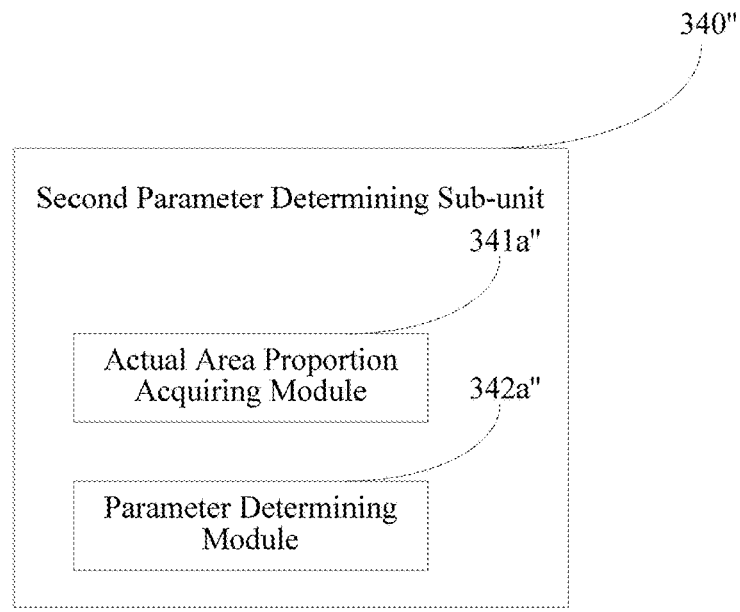
FIG. 3k is an example structural diagram of a module of the second parameter determining sub-unit in an embodiment of this application.

Specifically, as shown in FIG. 3k, in an optional implementation, the second parameter determining sub-unit 340" may comprise:

an actual area proportion acquiring module 341a" configured to acquire the actual area proportion of the fundus images of the gazing object on the fundus. Wherein, the area of the user's fundus is generally fixed, after the user's fundus images are collected, the images in the central fovea area of the yellow spot may be extracted therefrom and used as the fundus images of the gazing object, such that the area of the fundus images of the gazing object may be acquired and then the actual area proportion of the fundus images of the gazing object on the fundus may be acquired.

a parameter determining module 342a" configured to determine the scaling parameter of the corresponding sub-areas according to the actual area proportion. Wherein, the scaling parameter of the corresponding sub-areas determined according to the actual area proportion may be a magnification, and there are various modes configured to determine the corresponding magnification according to the actual area proportion; for example, the corresponding magnification is determined according to the piecewise function corresponding to the actual area proportion or by looking up the table. This implementation selects a quick way of looking up table, i.e., presetting a corresponding relation table between the actual area proportion and the magnification, and then determining the currently needed magnification by looking up the table during the implementation of the method. Wherein, the corresponding relation table between the actual area proportion and the magnification is shown in Table 2, and the details are not described here again.

Figure 3L:
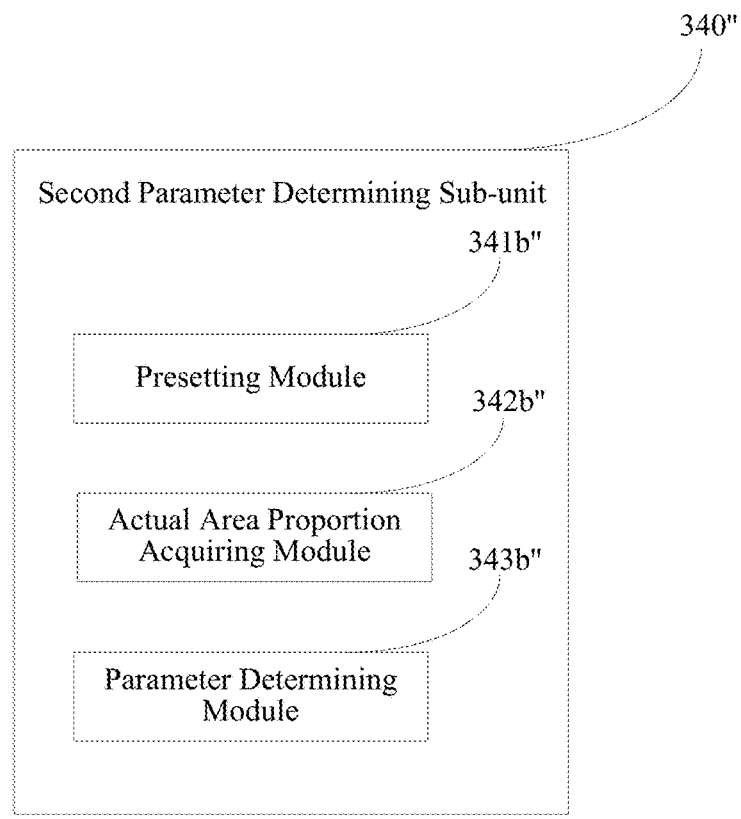
FIG. 3L is an example structural diagram of another module of the second parameter determining sub-unit in an embodiment of this application.

As shown in FIG. 3L, in another optional implementation, the second parameter determining sub-unit 340" may comprise:

a presetting module 341b''' configured to preset the target area proportion of the fundus images of the gazing object on the fundus and the buffer of the target area proportion. Wherein, the target area proportion is the area proportion of the fundus images of the gazing object on the fundus expected to achieve, such as 50%. Under the circumstance that the area proportion of the fundus images of the gazing object on the fundus is the target area proportion, the user will feel that the distance from the gazing object to himself or herself is moderate and the fundus images will be neither too large nor too small. Besides, the area proportion of the fundus images of the gazing object that makes the user feel comfortable is generally not an area proportion point, but rather an area proportion range; accordingly, the buffer of the target area proportion is also arranged in the mode g. Generally, the buffer is the area proportion range preset between both sides of the target area proportion. For example, assuming that the target area proportion is $S_T$, the buffer may be $((S_T-S_L, S_T) \cup (S_T, S_T+S_R))$, wherein, $S_T$, $S_L$ and $S_R$ are constants. Consequently, the region of area proportion $(S_T-S_L, S_T+S_R)$ is set as the region of area proportion that makes the user feel comfortable. $S_L$ may be equal to $S_R$; in this case, the third sub-buffer $(S_T-S_L, S_T)$ and the fourth sub-buffer $(S_T, S_T+S_R)$ of the buffer are of equal size and take $S_T$ as the center; and $S_L$ may also be unequal to $S_R$; in this case, the third sub-buffer $(S_T-S_L, S_T)$ and the fourth sub-buffer $(S_T, S_T+S_R)$ vary in size.

an actual area proportion acquiring module 342b''' configured to acquire the actual area proportion of the fundus images of the gazing object on the fundus. The actual area proportion acquiring module may be the same as that in the above implementation, and the details are not described here.

a parameter determining module 343b''' configured to determine the scaling parameter of the corresponding sub-areas according to the target area proportion, the actual area proportion and the buffer.

Wherein, in the step of determining the scaling parameter of the corresponding sub-areas according to the target area proportion, the actual area proportion and the buffer, for the scaling parameter:

In the case that the actual area proportion is less than the target area proportion and the actual area proportion is beyond the buffer, after the scaling property of the corresponding sub-areas is adjusted according to the scaling parameter, the fundus images of the gazing object may be amplified to the target area proportion.

In the case that the actual area proportion is greater than the target area proportion and the actual area proportion is beyond the buffer, after the scaling property of the corresponding sub-areas is adjusted according to the scaling parameter, the fundus images of the gazing object may be shrunk to the target area proportion.

In some implementations demanding simple control, the buffer may also be set at zero, i.e., it is equivalent to not setting the buffer, meanwhile equivalent to determining the scaling parameter of the corresponding sub-areas according to the target area proportion and the actual area proportion, and for the scaling parameter:

In the case that the actual area proportion is less than the target area proportion, after the scaling property of the corresponding sub-areas is adjusted according to the scaling parameter, the fundus images of the gazing object may be amplified to the target area proportion.

In the case that the actual area proportion is greater than the target area proportion, after the scaling property of the corresponding sub-areas is adjusted according to the scaling parameter, the fundus images of the gazing object may be shrunk to the target area proportion.

Figure 4:
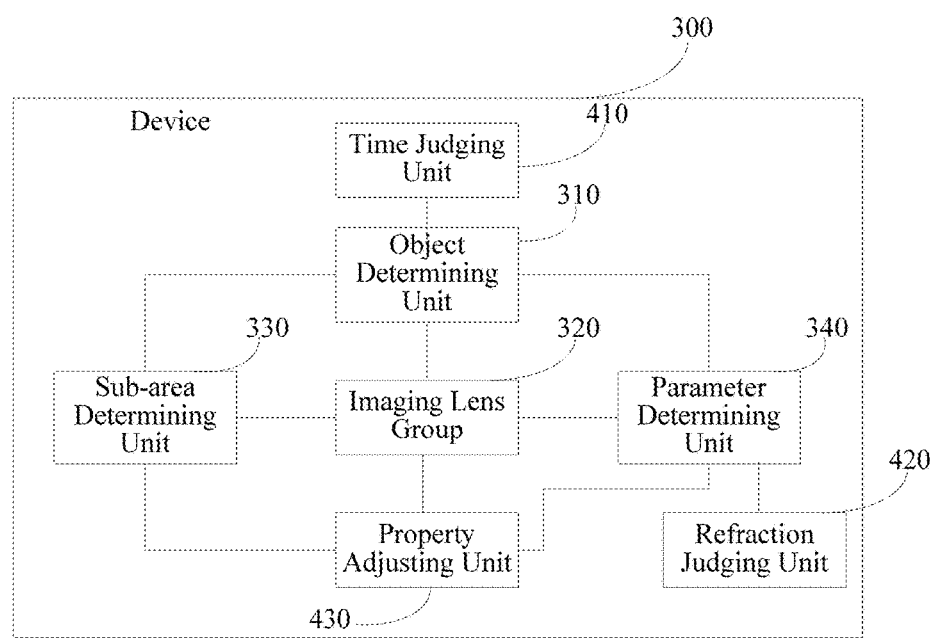
FIG. 4 is an example structural diagram of a module of another implementation of the imaging device for local scaling in an embodiment of this application.

In order to avoid the condition that the fundus images of the user is changed in ungazing state, such as random sweeping, to affect the user experience, as shown in FIG. 4, the device may also comprise:

a time judging unit 410 configured to judge whether the time for the eye to observe the gazing object exceeds the predetermined time, and if it exceeds the predetermined time, enabling the sub-areas determining unit 330, the imaging lens group 320 and the parameter determining unit 340.

Wherein, the predetermined time shall be set in such a manner to just make sure that the user is gazing the current observation object, and generally, when human eyes view a target, an optical impression may be obtained with the minimum observation time of 0.07-0.3 s, and the predetermined time shall be more than the minimum observation time; for example, it may be set at 1 s, 2 s, etc. In addition, the time for the user to observe the gazing object may be obtained by monitoring the time that the position of the focus point of the user's eye remains unchanged, and in the case that the time that the position of the focus point of the user's eye remains unchanged exceeds the predetermined time, it can be judged that the user is gazing the object currently in the position of the focus point, or obtained by monitoring the dwell time of the corresponding image in the central fovea of the yellow spot, and in the case that the dwell time of the corresponding image of the same object in the central fovea exceeds the predetermined time, it can be judged that the user is gazing the object currently.

When the gazing object is a mobile object, the judgment is only made in the beginning on whether the time for the eye to observe the mobile object exceeds the predetermined time, once the time is judged to exceed the predetermined time, the sub-area determining unit 330, the imaging lens group 320 and the parameter determining unit 340 are enabled, and when the user's line-of-sight follows the mobile object, the judgment would not be performed again on whether the gazing time exceeds the predetermined time as long as the user's eye are gazing the mobile object all the time (the user needs not to turn the head but to move eyeballs only), thereby facilitating the user in observing the scaling of the mobile object.

In addition, human eyes may have ametropia problems such as farsightedness, nearsightedness and/or astigmatism, therefore, the device also comprises:

a refraction judging unit 420 configured to judge whether the eye have ametropia problems and generating the ametropia information about the eye if the eye have ametropia problems;

Correspondingly, the parameter determining unit 340 configured to determine the scaling parameter of the corresponding sub-areas according to the gazing object and the ametropia information.

In addition, in order to adjust the imaging lens group 320, the device also comprises:

a property adjusting unit 430 configured to adjust the scaling property of the corresponding sub-areas according to the scaling parameter.

Figure 5A:
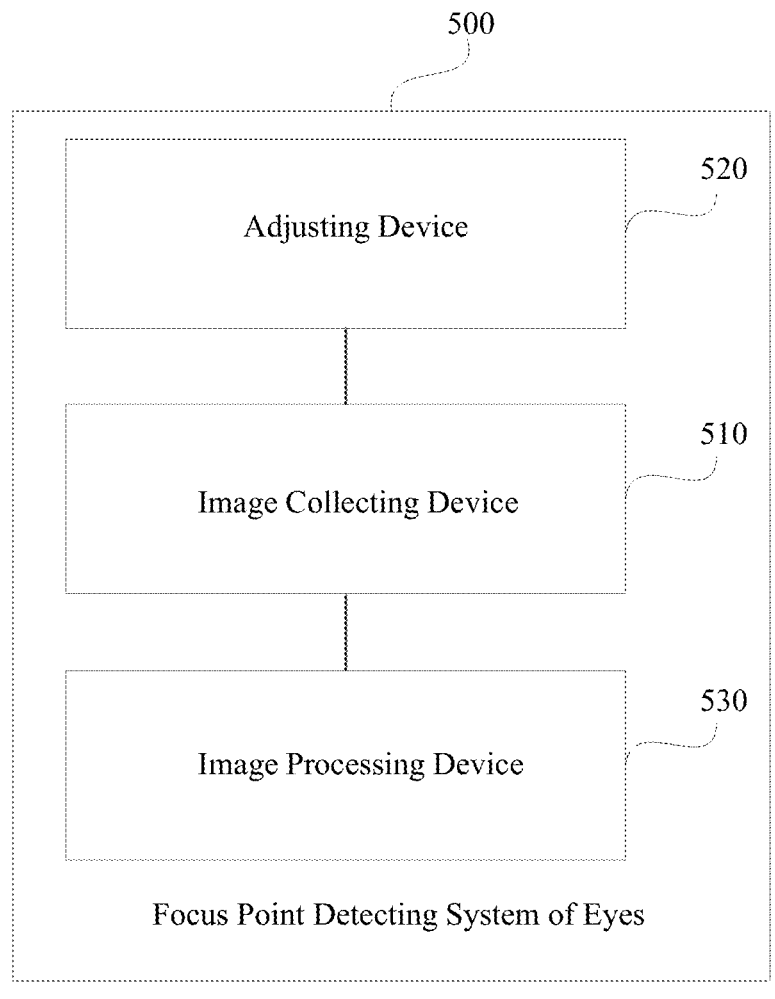
FIG. 5a is an example structural diagram of a module of an implementation of the focus point detecting system of an eye in an embodiment of this application.

As shown in FIG. 5a, the above mentioned focus point detecting system of an eye is described as follows, the focus point detecting system of the eye 500 may comprise:

an image collecting device 510 configured to collect the image presented on the fundus;

an adjusting device 520 configured to adjust the imaging parameter between the eye and the image collecting device 510 so that the image collecting device 510 obtains an image with the definition greater than the preset value;

an image processing device 530 configured to process the image obtained by the image collecting device 510, in order to obtain the optical parameter of the eye corresponding to the image with the definition greater than the preset value.

The system 500 obtains the optical parameter of the eye corresponding to the image with the definition greater than the preset value by analyzing and processing the fundus images, thereby calculating the current position of the focus point of the eye.

The images presented on the "fundus" herein are mainly the images presented on the retina, which may be the images of the fundus itself or images of other objects projected to the fundus.

Figure 5B:
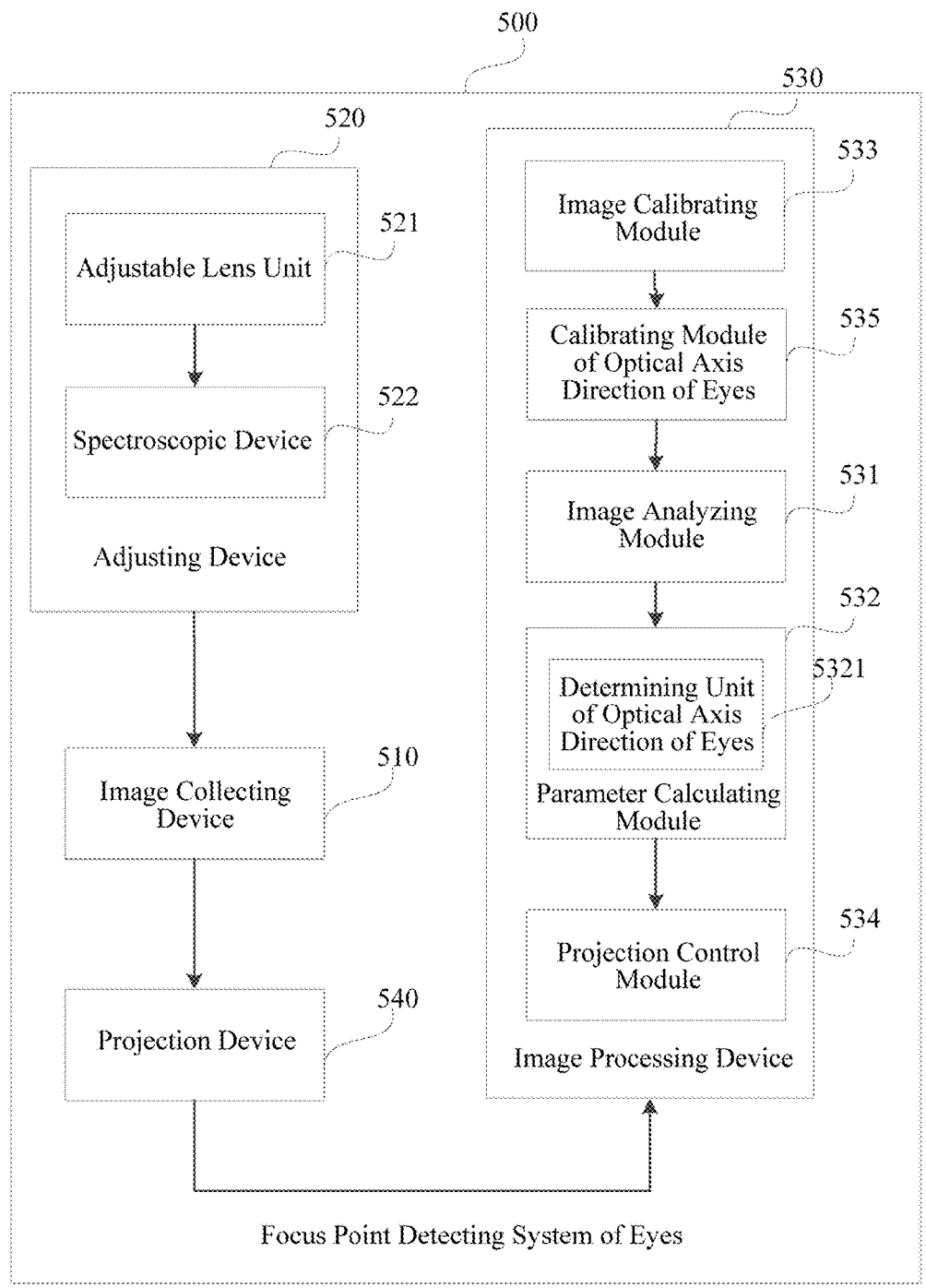
FIG. 5b is an example structural diagram of a module of another implementation of the focus point detecting system of an eye in an embodiment of this application.

As shown in FIG. 5b, in a possible implementation, the image collecting device 510 is a micro-camera, and in another possible implementation of the embodiment of this application, the image collecting device 510 may also adopt a photosensitive imaging device directly, such as devices like CCD (Charge Coupled Device) or CMOS (Complementary Metal Oxide Semiconductor).

In a possible implementation, the adjusting device 520 comprises: an adjustable lens unit 521 located in the optical path between the eye and the image collecting device 510 with adjustable focal length of itself and/or adjustable position in the optical path. Through the adjustable lens unit 521, the equivalent focal length of the system between the eye and the image collecting device 510 may be adjusted, and through the adjustment by the adjustable lens unit 521, the image collecting device 510 obtains the clearest image on the fundus in a certain position or status of the adjustable lens unit 521. In this implementation, the adjustable lens unit 521 performs continuous and real-time adjustment in the detection process.

Wherein, in a possible implementation, the adjustable lens unit 521 is: a focal length adjustable lens configured to adjust the focal length of itself by adjusting the refractivity and/or shape of itself. Specifically: 1) adjusting the focal length by adjusting the curvature of at least one plane of the focal length adjustable lens, for example, adding or reducing the liquid medium in the cavity formed by the double-layer transparent layer to adjust the curvature of the focal length adjustable lens; 2) adjusting the focal length by changing the refractivity of the focus adjustable lens, for example, for the focus adjustable lens filled with specific liquid crystal media, adjusting the arrangement mode of the liquid crystal medium by adjusting the voltage of electrodes corresponding to the liquid crystal medium, thereby changing the refractivity of the focal length adjustable lens.

In another possible implementation, the adjustable lens unit 521 comprises: a lens group configured to adjust the relative position between the lenses of the lens group to adjust the focal length of the lens group.

In addition to the two methods above mentioned for changing the optical path parameter of the system by adjusting the property of the adjustable lens unit 521, the optical path parameter of the system may also be changed by adjusting the position of the adjustable lens unit 521 in the optical path.

Wherein, in a possible implementation, in order not to affect the viewing experience of the user on the observation object and in order to apply portably the system to the wearable device, the adjusting device 520 also comprises: a spectroscopic device 522 configured to form the light transmission paths between the eye and the observation object as well as between the eye and the image collecting device 510. Thereby folding the optical path, reducing the system volume and avoiding affecting other experiences of the user as far as possible.

Wherein, in this implementation, the spectroscopic device comprises: a first spectroscopic unit located between the eye and the observation object configured to transmit the light from the observation object to the eye and transfer the light from the eye to the image collecting device.

The first spectroscopic unit may be a spectroscope, a spectroscopic optical waveguide (comprising optical fiber) or other suitable spectroscopic devices.

In a possible implementation, the image processing device 530 of the system comprises an optical path calibrating module configured to calibrate the optical path of the system, for example, performing the alignment and calibration for the optical axis of the optical path, in order to ensure the accuracy of the measurement.

In a possible implementation, the image processing device 530 comprises:

an image analyzing module 531 configured to analyze the image acquired by the image collecting device to find out the image with the definition greater than the preset value; and a parameter calculating module 532 configured to calculate the optical parameter of the eye based on the image with the definition greater than the preset value as well as the known imaging parameter of the system corresponding to the image with the definition greater than the preset value.

In this implementation, the image collecting device 510 can acquire the image with the definition greater than the preset value through the adjusting device 520, but it is required that the image with the definition greater than the preset value is found through the image analyzing module 531, and then, the optical parameter of the eye can be calculated based on the image with the definition greater than the preset value and the known optical path parameter of the system. The optical parameter of the eye herein may comprise the optical axis direction of the eye.

In a possible implementation of the embodiment of this application, the system also comprises: a projection device 540 configured to project the facula to the fundus. In a possible implementation, the functions of the projection device can be realized through a micro-projector.

The projected facula herein may have no specific pattern which is only configured to illuminate the fundus.

In a preferable implementation, the projected facula comprises a pattern with rich characteristics. Rich characteristics of the pattern may facilitate the detection, increasing the accuracy of detection. FIG. 5e shows an exemplary diagram of a facula pattern 550, and the pattern may be formed by the facula pattern generator such as frosted glass; FIG. 5f shows the fundus images taken when the facula pattern 550 is projected.

In order not to affect the normal view of the eye, preferably, the facula is the infrared facula invisible to the eye.

At this moment, in order to reduce the interference of other spectra:

The emergent surface of the projection device may be provided with a transmission filter of the light invisible to the eye.

The incident plane of the image collecting device may be provided with a transmission filter of the light invisible to the eye.

Wherein, in a possible implementation, the image processing device 530 also comprises:

a projection control module 534 configured to control the brightness of the projected facula of the projection device according to the results obtained by the image analyzing module.

For example, the projection control module 534 can adaptively adjust the brightness according to the characteristics of the images obtained by the image collecting device 510. The characteristics of the images herein comprise the contrast of the image features and the texture feature.

A special condition configured to control the brightness of projected facula of the projection device is to open or close the projection device; for example, the projection device can be periodically closed when the user continues to gaze at one point; When the user's fundus is bright enough, the light emitting source can be closed to detect the distance from the current focus point of the line-of-sight to the eye by only the fundus information.

In addition, the projection control module 534 may further control the brightness of projected facula of the projection device according to the ambient light.

Wherein, in a possible implementation, the image processing device 530 may also comprise: an image calibrating module 533 configured to calibrate the fundus images to obtain at least one reference image corresponding to the image presented on the fundus.

The image analysis unit 531 contrast the image acquired by the image collecting device 530 with the reference image, thereby acquiring the image with the definition greater than the preset value. Here, the images with the definition greater than the preset value can be images obtained with the minimum difference from the reference image. In this implementation, the difference between the currently acquired image and the reference image is calculated by the existing image processing algorithm such as an automatic focusing algorithm using the classical phase differences.

Wherein, in a possible implementation, the parameter calculating module 532 comprises:

a determining unit of optical axis direction of the eye 5321 configured to obtain the optical axis direction of the eye according to the characteristics of the eye corresponding to the image with the definition greater than the preset value. The line-of-sight direction may be obtained according to the optical axis direction of the eye and the fixed angle between the optical axis direction of the eye and the line-of-sight direction.

The characteristics of the eye herein can be obtained from the image with the definition greater than the preset value or acquired additionally.

Figure 5C:
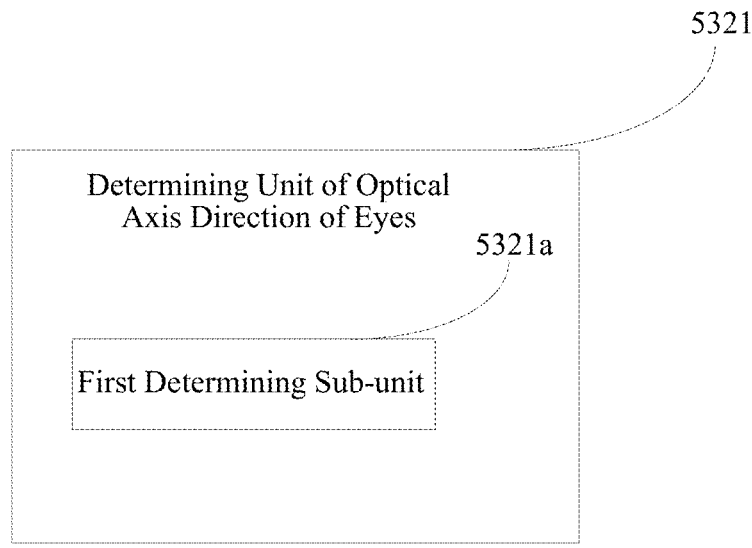
FIG. 5c is an example structural diagram of a module of the determining unit of optical axis direction of an eye in an embodiment of this application.

Wherein, as shown in FIG. 5c, in a possible implementation, the determining unit of optical axis direction of the eye 5321 comprises: a first determination sub-unit 5321a configured to obtain the optical axis direction of the eye according to the characteristics of the fundus corresponding to the image with the definition greater than the preset value. Compared with the optical axis direction of the eye obtained through the surface characteristics of pupils and eyeballs, the optical axis direction of the eye is determined in a higher accuracy through the characteristics of the fundus.

When the facula pattern is projected to the fundus, the size of the facula pattern may be larger than or smaller than the visible area in the fundus, wherein:

When the area of the facula pattern is smaller than or equal to that of the visible area, the classical feature points match algorithm (such as Scale Invariant Feature Transform (Scale Invariant Feature Transform, SIFT) algorithm) can be used to determine the optical axis direction of the eye by detecting the position of the facula pattern on the image relative to the fundus;

when the area of the facula pattern is greater than or equal to the visible area of the fundus, the optical axis direction of the eye can be determined through the position of the facula pattern on the obtained image relative to the original facula pattern (obtained through the image calibrating module), thereby determining the line-of-sight direction of the user.

Figure 5D:
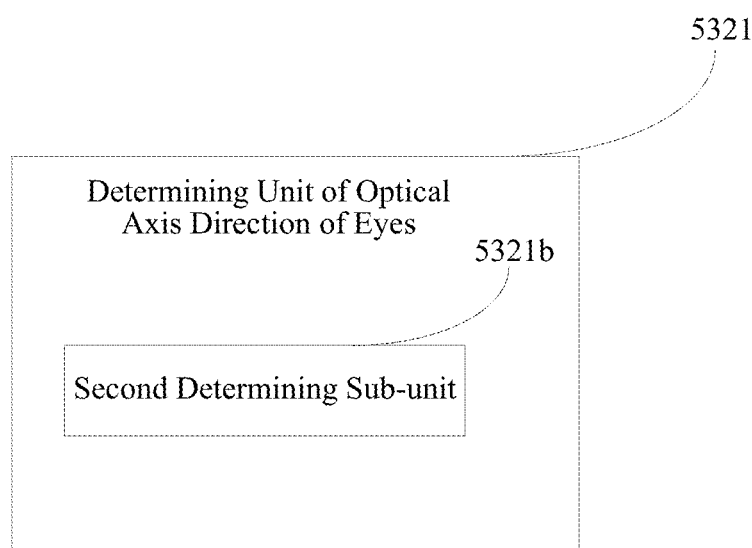
FIG. 5d is an example structural diagram of another module of the determining unit of optical axis direction of an eye in an embodiment of this application.
Figure 5E:
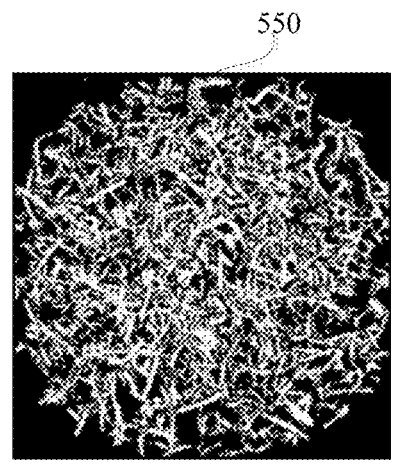
FIG. 5e is an example diagram of a facula pattern in an embodiment of this application.
Figure 5F:
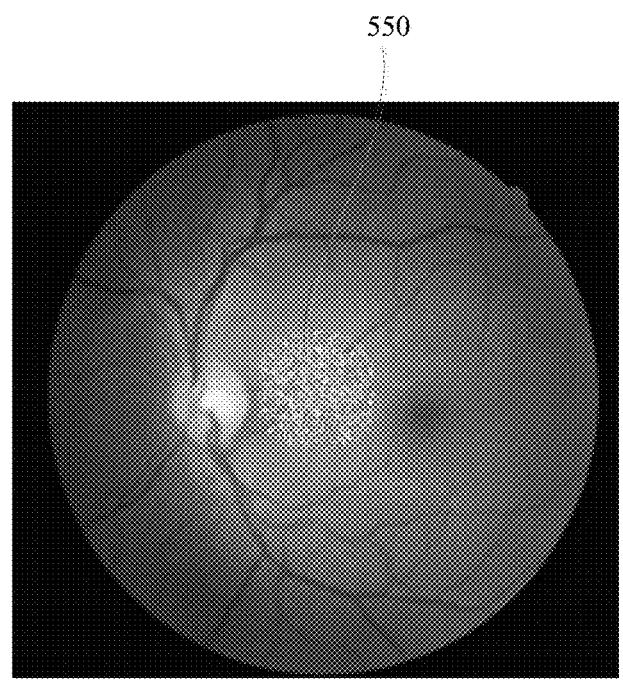
FIG. 5f is an example fundus image captured when the facula pattern is projected in an embodiment of this application.

As shown in FIG. 5d, in another possible implementation, the determining unit of the optical axis direction of the eye 5321 comprises: a second determination sub-unit 5321b configured to obtain the optical axis direction of the eye according to the characteristics of the eye's pupils corresponding to the image with the definition greater than the preset value. The characteristics of pupils of the eye herein may be acquired from the image with the definition greater than the preset value or acquired additionally. Obtaining the optical axis direction of the eye through the characteristics of the eye's pupils is the prior art, so it is not repeated herein.

Wherein, as shown in FIG. 5b, in a possible implementation, the image processing device 530 also comprises: a calibrating module of optical axis direction of the eye 535 configured to calibrate the optical axis direction of the eye, in order to determine the optical axis direction of the eye more accurately.

In this implementation, the known imaging parameter of the system comprises the fixed imaging parameter and the real-time imaging parameter, wherein the real-time imaging parameter is the parameter information of the adjustable lens unit corresponding to the image with the definition greater than the preset value, and the parameter information can be obtained by real-time recording when the image with the definition greater than the preset value is acquired.

Figure 5G:
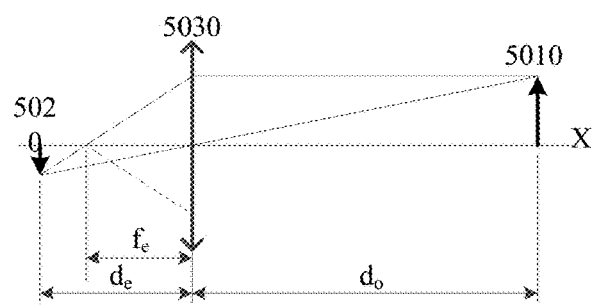
FIG. 5g is an example diagram of eye imaging in an embodiment of this application.

After the current optical parameter of the eye is obtained, the distance from the focus point of the eye to the eye may be calculated as follows:

FIG. 5g shows a schematic diagram of the eye imaging, and in combination with the lens imaging formula in the classical optical theory, the formula (1) can be obtained from FIG. 5g:

$$\frac{1}{d_o} + \frac{1}{d_e} = \frac{1}{f_e} \tag{1}$$

wherein, $d_o$ and $d_e$, are the distances from the current observation object 5010 of the eye and the real image 5020 on the retina to the equivalent lens 5030 of the eye respectively, $f_e$ is the equivalent focal length of the equivalent lens 5030 of the eye and X is the line-of-sight direction of the eye.

Figure 5H:
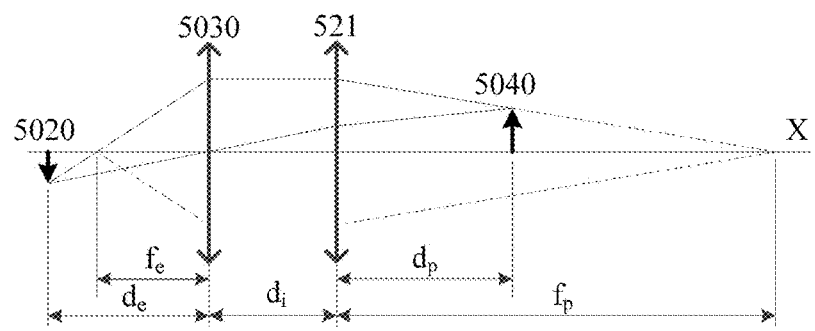
FIG. 5h is an example diagram of a distance from the focus point of an eye to the eye acquired according to the known optical parameter of the system and the optical parameter of the eye in this application.

FIG. 5h shows a schematic diagram of obtaining the distance from the focus point of the eye to the eye according to the known optical parameter of the system and the optical parameter of the eye, the facula 5040 in FIG. 5h may form a virtual image through the adjustable lens unit 521; and assuming that the distance from the virtual image to the lens is x, the system of equations may be obtained by combining the formula (1) as follows:

$$\begin{cases} \dfrac{1}{d_p} - \dfrac{1}{x} = \dfrac{1}{f_p} \\ \dfrac{1}{d_i + x} + \dfrac{1}{d_e} = \dfrac{1}{f_e} \end{cases} \tag{2}$$

Wherein, $d_p$ is the optical equivalent distance from the facula 5040 to the adjustable lens unit 521; $d_1$ is the optical equivalent distance from the adjustable lens unit 521 to the equivalent lens 5030 of the eye; $f_p$ is the value of the focal length of the adjustable lens unit 521; and $d_1$ is the distance from the equivalent lens 5030 of the eye to the adjustable lens unit 521.

From formulas (1) and (2), the distance $d_o$ from the current observation object 5010 (focus point of the eye) to the equivalent lens 5030 of the eye (i.e. the actual distance of focus point of the eye) can be obtained, as shown in formula (3):

$$d_o = d_i + \frac{d_p \cdot f_p}{f_p - d_p} \quad (3)$$

According to the actual distance of focus point of the eye and the line-of-sight, the position of the focus point of the eye may be obtained.

Figure 6:
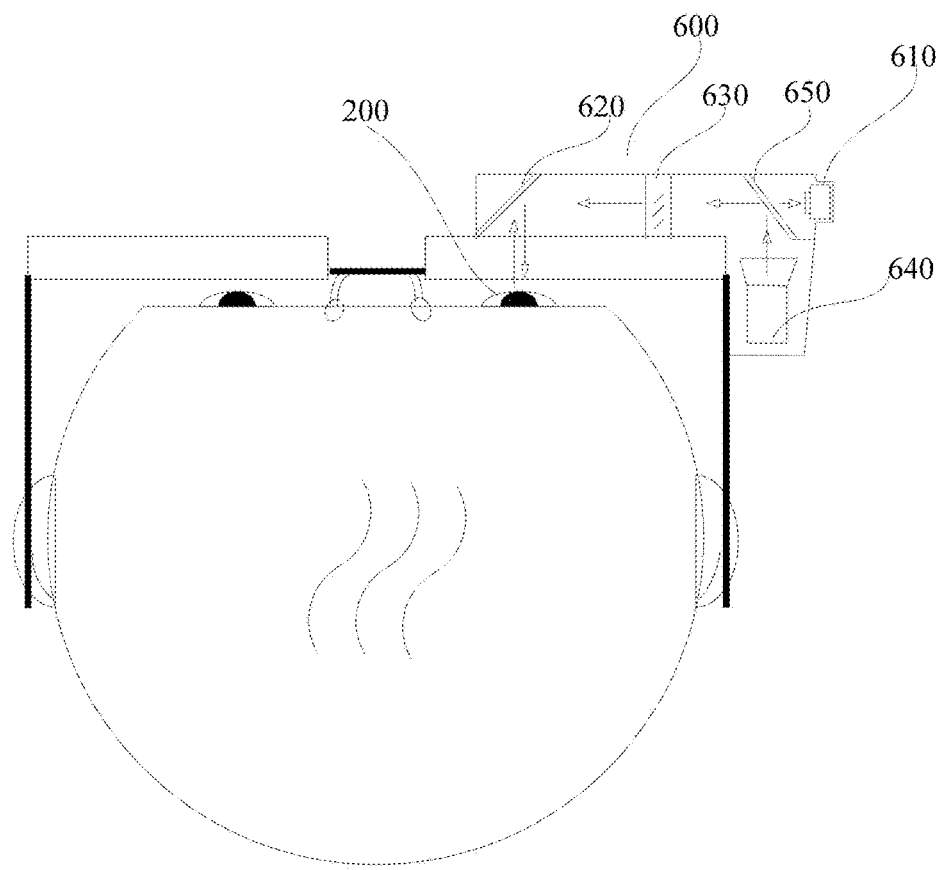
FIG. 6 is an example diagram of a specific example when the focus point detecting system of an eye is applied to glasses in an embodiment of this application.

FIG. 6 shows a diagram of a specific example when the focus point detecting system of the eye 600 is applied to glasses in an embodiment of this application. The focus point detecting system of the eye 600 can be configured to realize the function of the first focus point detecting module.

Wherein, the function of the micro-camera 610 is the same as that of the image collecting device in FIG. 5b, and in order to not affect the line-of-sight for the user to normally view the object, the micro-camera is arranged on the right outboard of the glasses;

the function of the first spectroscope 620 is the same as that of the first spectroscopic unit shown in FIG. 5b, and the first spectroscope 620 is arranged at the intersection of the gazing direction of the eye and the incidence direction of the camera 610 at a certain angle of inclination, to transmit the light of the gazing object entering the eye 200 and reflect the light from the eye 200 to the camera 610; and the function of the focal length adjustable lens 630 is the same as that of the focal length adjustable lens in FIG. 5b, and the focal length adjustable lens is located between the first spectroscope 620 and the camera 610 to adjust the focal length value in real time, such that the camera 610 can capture the clearest image on the fundus at a certain focal length value.

In this implementation, the image processing device is not shown in FIG. 6, and the function thereof is the same as that of the image processing device shown in FIG. 5b.

Generally, the fundus is not bright enough, so it is better to illuminate the fundus, and in this implementation, the fundus is illuminated by a light emitting source 640. In order not to influence users' experience, the preferable light emitting source 640 herein may be the light invisible to the eye, therefore, a near-infrared light emitting source which may have a weak impact on the eye 200 and is relatively sensitive to the camera 610 is preferable.

In this implementation, the light emitting source 640 is located on the outside of the right eyeglasses frame, so the light emitted by the light emitting source 640 may be transmitted to the fundus through a second spectroscope 650 and the first spectroscope 620 together. In this implementation, the second spectroscope 650 is also located in front of the incident plane of the camera 610, so the light from the fundus to the second spectroscope 650 is also required to be transmitted.

It can be seen that in this implementation, in order to improve users' experience and enhance the clarity of collection of the camera 610, the first spectroscope 620 may have the property of high infrared reflectivity and high transmission rate of visible light. For example, the above property may be achieved by arranging an infrared reflective film on the side of the first spectroscope 620 toward the eye 200.

It can be seen from FIG. 6 that in this implementation, the focus point detecting system of the eye 600 is located on the side of glasses lenses away from the eye 200, so the lens may be regarded as a part of glasses when the eye optical parameter is calculated, without knowing about the optical property of the lens.

In other implementations of the embodiment of this application, the focus point detecting system of the eye 600 may be located on the side of the glasses lenses near the eye 200, and in this case, it is required that the optical property parameter of the lens is obtained in advance and the influencing factors of the lens are considered when the distance of the focus point is calculated.

The light emitted from the light emitting source 640 passes through the glasses lenses and enters users' eye through the reflection of the second spectroscope 650, the projection of the focal length adjustable lens 630 and the reflection of the first spectroscope 620, and finally arrives at the retina of fundus; The camera 610 captures the image on the fundus through the optical path formed by the first spectroscope 620, the focal length adjustable lens 630 and the second spectroscope 650 by passing through the pupil of the eye 200.

Figure 7A:
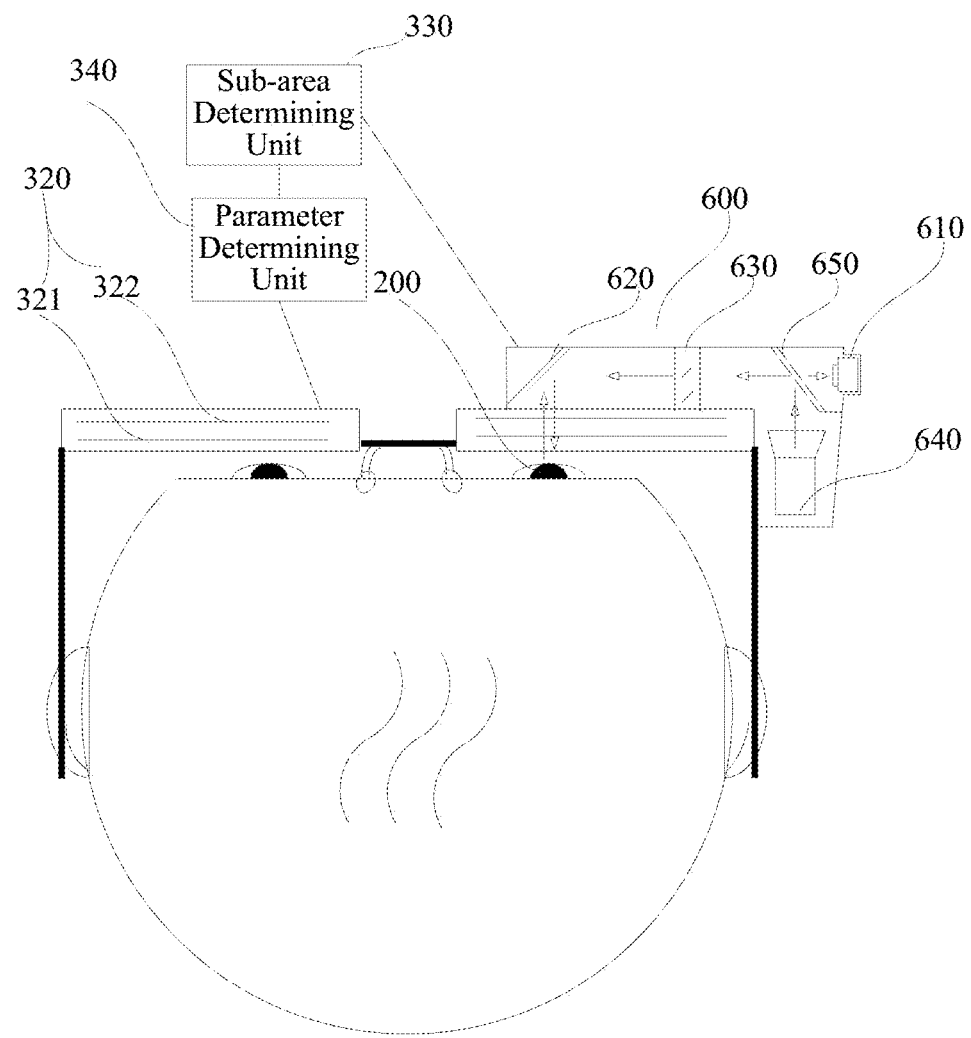
FIG. 7a is an example diagram of a specific example when the imaging device for local scaling is applied to glasses in an embodiment of this application.

FIG. 7a is a schematic diagram of a specific example when the device of the embodiment of this application is applied to the glasses, wherein, the glasses may be both ordinary glasses or optical devices such as helmet, front windshield and contact lens. As shown in FIG. 7a, the glasses of the embodiment use the focus point detecting system of the eye 600 to determine the gazing object of the eye, i.e., realizing the function of the object determining unit 310, and the realization of the focus point detecting system of the eye 400 is not repeated.

Wherein, the imaging lens group 320 is arranged in the lens, and comprises at least two lenses and is divided into a plurality of sub-areas, and the part of the at least two lenses corresponding to the sub-areas being adjustable in the scaling property. For simplicity, the imaging lens group 320 in FIG. 7a comprises the first lens 321 on the side near the eye and the second lens 322 on the side near the gazing object.

Wherein, the scaling property may be adjusted by changing the focal lengths of the at least two lenses respectively, and the focal lengths may be adjusted in the following methods: 1) adjusting the focal length by adjusting the curvature of at least one plane of the lens, for example, for the lens comprising a cavity formed by the double-layer transparent layer, adjusting the focal length by adding or reducing the liquid medium in the cavity formed by the double-layer transparent layer. In this case, the scaling parameter above mentioned, for example, may mean that the liquid medium is reduced or increased by a certain value; 2) adjusting the focal length by changing the refractivity of the lens, for example, for the lens filled with specific liquid crystal medium, adjusting the arrangement mode of the liquid crystal medium by adjusting the voltage of the electrode corresponding to the liquid crystal medium, thereby changing the refractivity of the lens. In this case, the scaling parameter above mentioned, for example, may mean that the voltage of the electrode is increased or reduced by a certain value.

In addition to the focal length above mentioned, the scaling property may also be adjusted by changing the relative position between the at least two lenses. Herein, the relative position between the lenses may be changed by adjusting the relative distance between the lenses in the optical axis direction, and/or the relative position between the lenses in the vertical optical axis direction, and/or the relative rotation angle around the optical axis.

Wherein, the first lens 321 may be set in such a manner that the curvature on the side toward user's eye 200 is adjustable, the second lens 322 is set in such a manner that the curvature on the side toward the gazing object is adjustable, and the positions of the first lens 321 and the second lens 322 is fixedly set, so that the glasses are simple in structure, lightweight and portable.

Figure 7B:
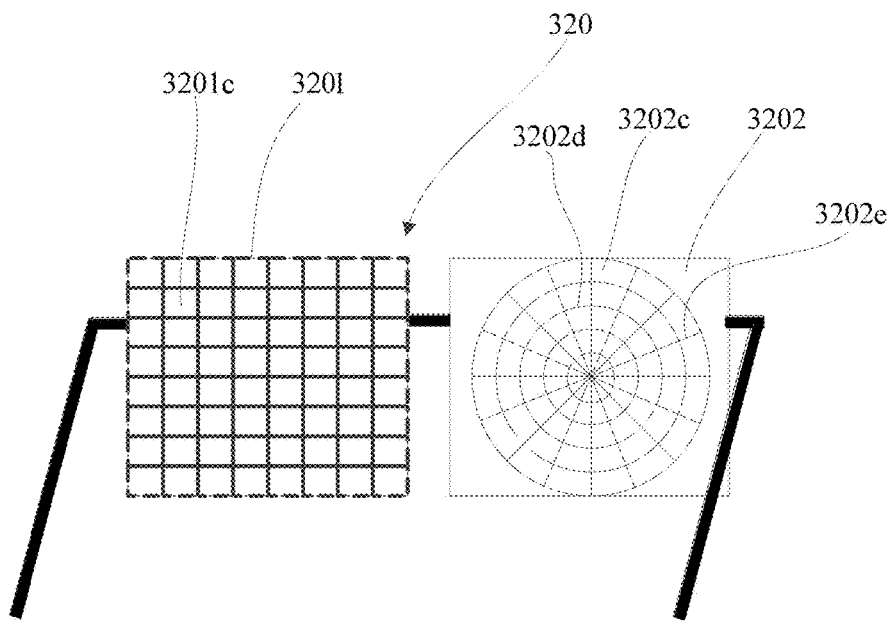
FIG. 7b is an example diagram of a sub-area when the imaging device for local scaling is applied to glasses in an embodiment of this application.

As shown by the first imaging lens group 3201 on the left of the glasses in FIG. 7b, in a possible implementation of the embodiment of this application, the plurality of sub-areas 3201c with adjustable scaling property are distributed in a rectangular array. In this embodiment, the sub-areas 3201c are of the same size with the rows and columns aligned; and in other embodiments, the sub-areas 3201c may also be set with unaligned rows and columns.

As shown by the second imaging lens group 3202 on the right of the glasses in FIG. 7b, the plurality of sub-areas 3202c with adjustable scaling property are distributed in a radial concentric circle (consisting of several concentric circles 3202d and several radial lines 3202e radially connecting adjacent concentric circles 3202d) array. In this embodiment, the radial lines 3202e of the radial concentric circles are aligned, and in other embodiments, the radial lines 3202e between two adjacent concentric circles 3202d may also be unaligned.

In FIG. 7b of the implementation, for description, two imaging lens groups 320 in sub-areas with different distributions are set in a pair of glasses, and in practical application, the left and right imaging lens groups 320 of a pair of glasses are generally the same or similar in the sub-area distribution.

Of course, it may be known to the technical personnel in the field that in addition to the rectangular array and the radial concentric circle array above, the sub-areas may also be distributed in other arrays or unarrayed mode.

The sub-area determining unit 330 is configured to determine the corresponding sub-areas according to the projection of the gazing object on the imaging lens group, wherein, the projection is a projection of the gazing object on the imaging lens group in the line-of-sight direction, and may be calculated according to the relative position between the imaging lens group 320 and the gazing object and the line-of-sight direction.

The parameter determining unit 340 may determine the scaling parameter of the corresponding sub-areas according to the actual viewing distance from the gazing object to the eye or the actual area proportion of the fundus images of the gazing object on the fundus, and see relevant description of step S230 in the method embodiment for the specific determination method.

Generally, the sub-area determining unit 330 and the parameter determining unit 340 may be realized by integrating into the same processor, thereby reducing the weight of the glasses and increasing the portability thereof. The processor may be a Central Processing Unit CPU, or a specific integrated circuit ASIC (Application Specific Integrated Circuit), or one or more integrated circuits configured to implement the embodiment of this application.

The property adjusting unit 430 is not shown in FIG. 7a, it generally adjusts the scaling property of the corresponding sub-areas by outputting the voltage or current signals corresponding to the scaling parameter to the imaging lens group 320.

In addition, the glasses may also comprise the time judging unit 410 and the refraction judging unit 420.

Wherein, the time judging unit 410 generally comprises a timer configured to monitor the time that the position of the focus point of user's eye remains unchanged, or monitoring the dwell time of the corresponding image in the central fovea of the yellow spot, and in the case that the time that the position of the focus point of user's eye remains unchanged exceeds the predetermined time; or, the dwell time of the corresponding image of the same object in the central fovea exceeds the predetermined time, it can be judged that the user is gazing the object currently.

The refraction judging unit 420 may be realized by using the existing refraction detecting device, and it is a prior art and the details are not described here.

Figure 8A:
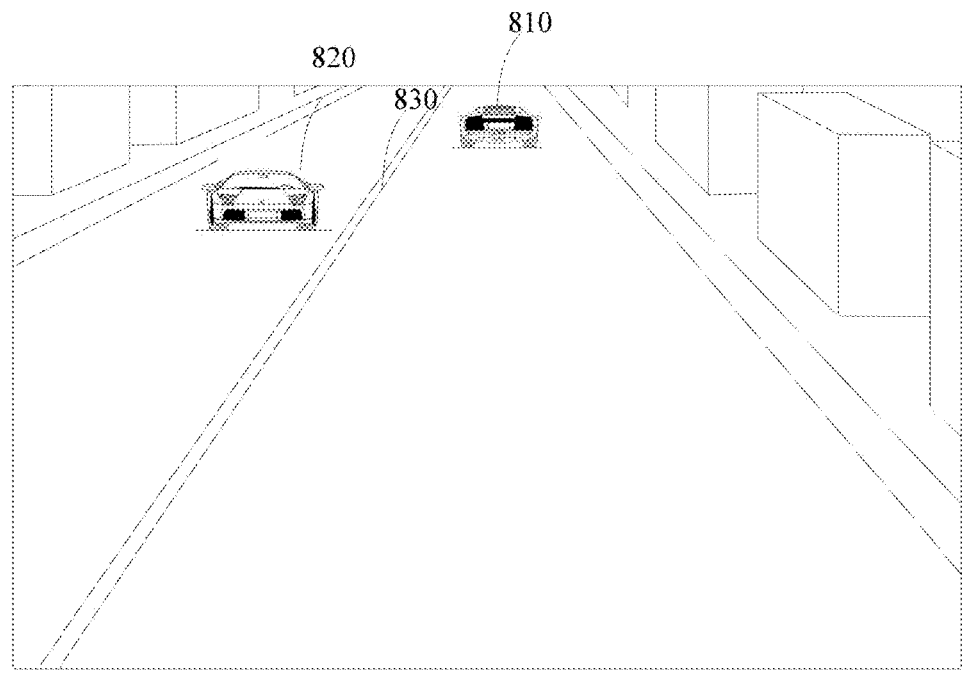
FIG. 8a and FIG. 8b are example diagrams of the application scenes of the imaging device for local scaling in an embodiment of this application.
Figure 8B:
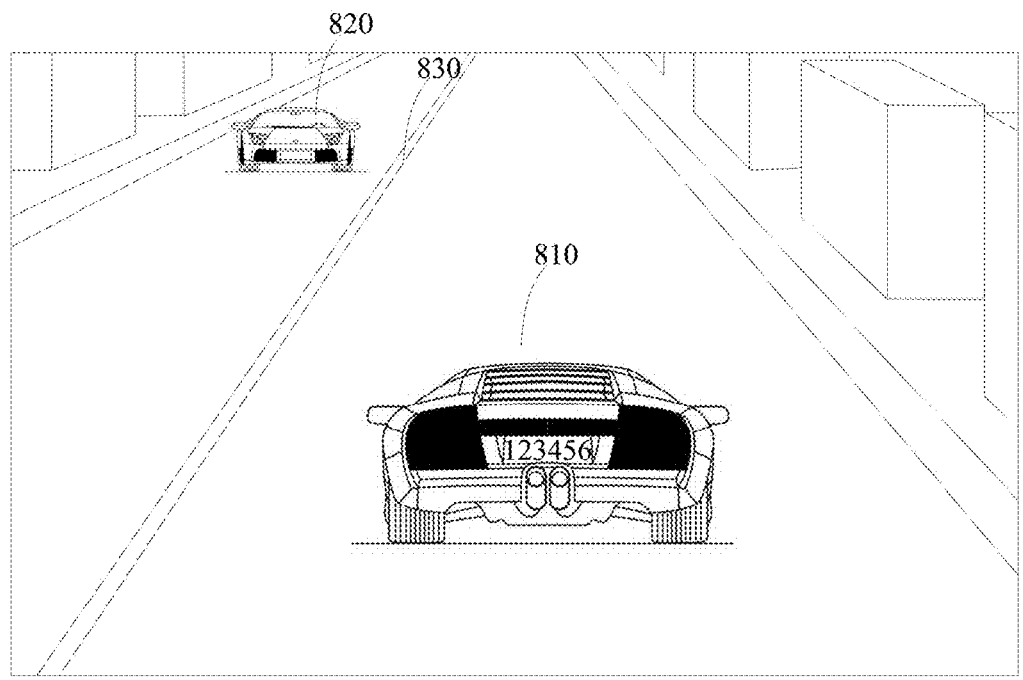

FIG. 8a and FIG. 8b are diagrams of this application scenes of the device 300 of this application. FIG. 8a is a schematic diagram of the original view of the user driving a car, wherein, the front car 810 is the car in front of the car driven by the user (not shown), the side car 820 is the car in side front of the car driven by the user, and the racing line 830 is the lane line between the car driven by the user and the side car 820. Assuming that the user demands to view carefully the license plate number of the front car 810 at this time to identify whether his/her friend is driving the car, but the front car 810 is at a distance of more than 100 m and the license plate number cannot be identified by naked eyes.

FIG. 8b is a schematic diagram of the view obtained through the device 300 by the user, it can be seen that the front car 810 is brought close and the license plate number thereof 123456 is clear, at the same time, the side car 820 and the racing line 830 are still in the view and keep the original distance from the car, thereby facilitating in increasing the driving safety of the user.

Figure 9:
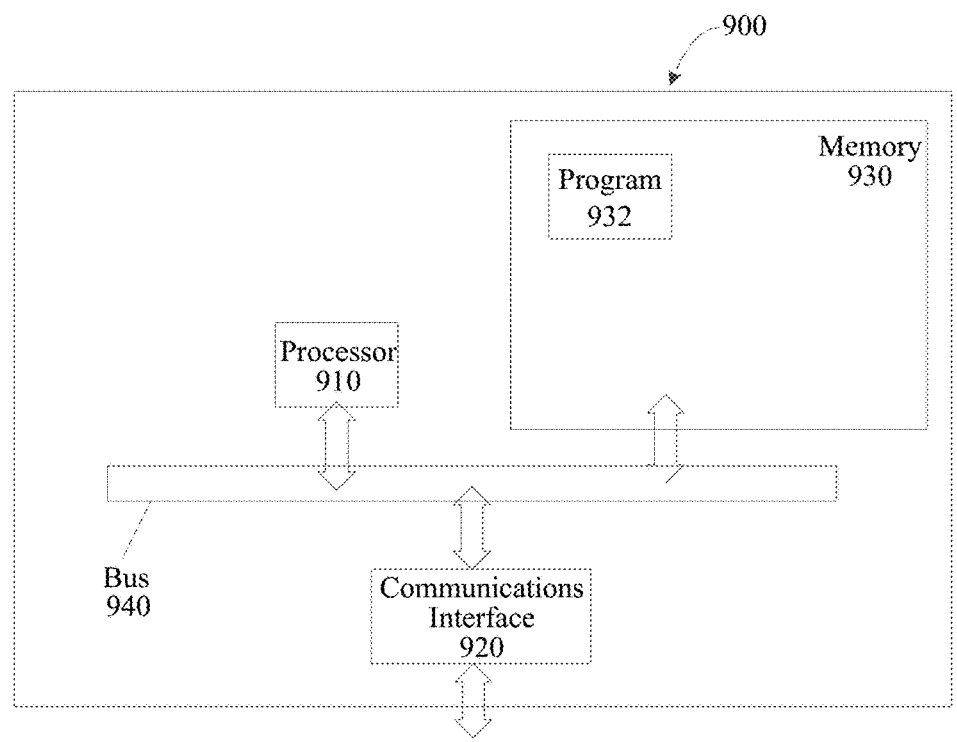
FIG. 9 is an example structural diagram of the imaging device for local scaling in an embodiment of the present invention.

The structure of the imaging device for local scaling of the embodiment of the present invention is shown in FIG. 9. The specific embodiment of the present invention is not intended to limit the specific implementation of the imaging device for local scaling, as shown in FIG. 9, the imaging device 900 may comprise:

a processor 910, a Communications Interface 920, a memory 930 and a communication bus 940. Wherein:

The processor 910, the communications interface 920 and the memory 930 complete the mutual communication through the communication bus 940.

The communications interface 920 is configured to communicate with other network elements.

The processor 910 is configured to implement the program 932, specifically, it can implement the relevant steps in the method embodiment shown in FIG. 9 above.

Specifically, the program 932 may comprise the program codes which comprise the computer operating instructions.

The processor 910 may be a Central Processing Unit CPU, or a specific integrated circuit ASIC (Application Specific Integrated Circuit), or one or more integrated circuits configured to implement the embodiment of the present invention.

The memory 930 is configured to store the program 932. The memory 930 may contain a high-speed RAM memory and may also comprise a non-volatile memory, such as at least one disk memory. Specifically, the program 932 may execute the following steps:

determining the gazing object of an eye;

determining the corresponding sub-areas of the imaging lens group according to the gazing object; the imaging lens group being configured to scale and image for the gazing object, comprising a plurality of sub-areas with adjustable scaling property;

and determining the scaling parameter of the corresponding sub-areas according to the gazing object.

For the specific implementation of the steps in the program 932, see the corresponding steps or modules in the above-mentioned embodiment, and the details are not described here. It may be clearly understood by persons skilled in the art that, for the purpose of convenient and brief description, for the detailed working process of the above mentioned device and module, refer to the corresponding process description in the above-mentioned method embodiment, and the details are not described here again. In summary, in the device of the embodiment, the user's fundus images of the gazing object can be scaled in a local scaling mode, so as to avoid changing the overall view of the user and to enable the user to conveniently observe the gazing object and to simultaneously correctly perceive the surrounding environment.

Common persons skilled in the art should appreciate that, in combination with the examples described in the embodiments here, units and method steps can be implemented by electronic hardware, or a combination of computer software and electronic hardware. Whether the functions are executed by hardware or software depends on the particular applications and design constraint conditions of technical schemes. Professional persons skilled in the art may use different methods to implement the described functions for each particular application, but it should not be considered that the implementation goes beyond the scope of this application.

When being implemented in the form of a software functional unit and sold or used as a separate product, the functions may be stored in a computer-readable storage medium. Based on this understanding, the technical scheme of this application, in essence, or the part contributing to the prior art or the part of the technical scheme may be embodied in the form of software product, and the computer software product is stored in a readable storage medium and comprises various instructions for enabling a computer apparatus (which may be a personal computer, a server, a network apparatus, etc.) to implement all or partial steps of the method of each embodiment of this application. However, the above-mentioned storage medium comprises any medium that may store program codes, such as a U-disk, a removable hard disk, a Read-Only Memory (ROM), a Random Access Memory (RAM), a magnetic disk, or an optical disk.

The above implementations are only used for illustrating this application, and not intended to limit this application, and various modifications and improvements may be made by the ordinary technical personnel in relevant technical field within the spirit and scope of this application; accordingly, all equivalent technical schemes belong to the scope of this application and the scope of patent protection of this application should be limited by Claims.

The invention claimed is:

1. A method, comprising:
    determining, by a system comprising a processor, a gazed object at which an eye is gazing;
    determining corresponding sub-areas of an imaging lens group according to the gazed object, the imaging lens group being configured to scale and image for the gazed object and comprising a plurality of sub-areas with adjustable scaling property; and
    determining a scaling parameter of the corresponding sub-areas according to the gazed object,
    wherein the determining the gazed object comprises:
        detecting a position of a focus point of the eye according to an optical parameter corresponding to images presented on the fundus and with a defined clarity determined to be greater than a preset value, wherein the optical parameter is the optical parameter of an optical path between an image collection position and the eye; and
        determining the gazed object according to the position of the focus point of the eye.

2. The method of claim 1, wherein the determining the position of the focus point of the eye according to the optical parameter corresponding to the images presented on the fundus and with the defined clarity determined to be greater than the preset value comprises:
    collecting fundus images;
    adjusting the imaging parameter of the optical path between the eye and the image collection position for collecting a set of images with the defined clarity determined to be greater than the preset value;
    processing the fundus images;
    acquiring the optical parameter of the eye according to an imaging parameter corresponding to the set of images with the defined clarity determined to be greater than the preset value, wherein the imaging parameter is the imaging parameter of the optical path between the image collection position and the eye; and
    determining the position of the focus point of the eye according to the optical parameter of the eye.

3. The method of claim 2, wherein the optical parameter of the eye comprises an equivalent focal length and a line-of-sight direction of the eye.

4. The method of claim 1, wherein the imaging lens group comprises at least two lenses, and the at least two lenses are adjustable in scaling property with respective portions of the corresponding sub-areas.

5. The method of claim 4, wherein the scaling property is adjusted by changing respective focal lengths of the at least two lenses.

6. The method of claim 4, wherein the scaling property is adjusted by changing a relative position between the at least two lenses.

7. The method of claim 1, wherein the plurality of sub-areas are distributed in an array.

8. The method of claim 1, wherein the determining the corresponding sub-areas of the imaging lens group according to the gazed object comprises:
    determining the corresponding sub-areas according to a projection of the gazed object on the imaging lens group.

9. The method of claim 1, wherein the determining the scaling parameter of the corresponding sub-areas according to the gazed object comprises:
    determining the scaling parameter of the corresponding sub-areas according to an actual viewing distance from the gazed object to the eye.

10. The method of claim 1, wherein the determining the scaling parameter of the corresponding sub-areas according to the gazed object comprises:
    determining the scaling parameter of the corresponding sub-areas according to an actual area proportion of the fundus images of the gazed object on the fundus.

11. The method of claim 1, further comprising:
determining whether a time for the eye to observe the gazed object exceeds a predetermined time, and in response to the time for the eye to view the gazed object being determined to exceed the predetermined time, determining the corresponding sub-areas of the imaging lens group according to the gazed object and determining the scaling parameter of the corresponding sub-areas according to the gazed object.

12. The method of claim 1, further comprising:
determining whether the eye has ametropia and generating ametropia information about the eye in response to the eye being determined to have ametropia,
wherein the determining the scaling parameter of the corresponding sub-areas according to the gazed object comprises:
determining the scaling parameter of the corresponding sub-areas according to the gazed object and the ametropia information.

13. The method of claim 1, further comprising:
adjusting the scaling property of the corresponding sub-areas according to the scaling parameter.

14. An imaging device, comprising:
an object determining unit configured to determine a gazed object of an eye;
an imaging lens group configured to scale and image for the gazed object, comprising a plurality of sub-areas with an adjustable scaling property;
a sub-area determining unit configured to determine corresponding sub-areas of the imaging lens group according to the gazed object; and
a parameter determining unit configured to determine a scaling parameter of the corresponding sub-areas according to the gazed object,
wherein the object determining unit comprises:
a first object determining sub-unit configured to detect a position of a focus point of the eye and determine the gazed object according to the position of the focus point of the eye,
wherein the first object determining sub-unit comprises:
a first focus point detecting module configured to determine the position of the focus point of the eye according to an optical parameter corresponding to images presented on a fundus and with a defined clarity determined to be greater than a preset value, wherein the optical parameter is the optical parameter of an optical path between an image collection position and the eye.

15. The imaging device of claim 14, wherein the first focus point detecting module comprises:
an image collecting sub-module configured to collect fundus images;
an image adjusting sub-module configured to adjust the optical parameter of the optical path between the eye and the image collection position and configured to collect a set of images with the defined clarity determined to be greater than a preset value;
an image processing sub-module configured to process the collected images; acquire the optical parameter of the eye according to an imaging parameter corresponding to the images with the defined clarity greater than the preset value; and
a focus point determining sub-module configured to determine the position of the focus point of the eye according to the optical parameter of the eye.

16. The imaging device of claim 14, wherein the imaging lens group comprises at least two lenses, and the at least two lenses are adjustable in scaling property with each portion of the corresponding sub-areas.

17. The imaging device of claim 14, wherein the plurality of sub-areas are distributed in an array.

18. The imaging device of claim 14, wherein the sub-area determining unit is configured to determine the corresponding sub-areas according to the projection of the gazed object on the imaging lens group.

19. The imaging device of claim 14, wherein the parameter determining unit comprises:
a first parameter determining sub-unit configured to determine the scaling parameter of the corresponding sub-areas according to an actual viewing distance from the gazed object to the eye.

20. The imaging device of claim 14, wherein the parameter determining unit comprises:
a second parameter determining sub-unit configured to determine the scaling parameter of the corresponding sub-areas according to an actual area proportion of fundus images of the gazed object on a fundus.

21. The imaging device of claim 14, wherein the device further comprises:
a time judging unit configured to determine whether a time for the eye to view the gazed object exceeds a predetermined time, and if the time for the eye to view the gazed object exceeds the predetermined time, enabling the sub-area determining unit, the imaging lens group and the parameter determining unit.

22. The imaging device of claim 14, wherein the device further comprises:
a refraction judging unit configured to determine whether the eye has ametropia problems and generate ametropia information of the eye if the eye has ametropia problems, and wherein the parameter determining unit is further configured to determine the scaling parameter of the corresponding sub-areas according to the gazed object and the ametropia information.

23. The imaging device of claim 14, wherein the device further comprises:
a property adjusting unit configured to adjust the scaling property of the corresponding sub-areas according to the scaling parameter.

24. The imaging device of claim 14, wherein the device is a pair of glasses.

25. A computer readable storage device, comprising at least one executable instruction, which, in response to execution, causes an imaging device comprising a processor to perform operations, comprising:
determining a gazed object of an eye;
determining corresponding sub-areas of an imaging lens group according to the gazed object; and
determining a scaling parameter of the corresponding sub-areas according to the gazed object,
wherein the determining the gazed object comprises:
detecting a position of a focus point of the eye according to an optical parameter corresponding to images presented on the fundus and with a defined clarity determined to be greater than a preset value, wherein the optical parameter is the optical parameter of an optical path between an image collection position and the eye; and
determining the gazed object according to the position of the focus point of the eye.

26. An imaging device, characterized by comprising a processor and a memory, the memory storing the executable instructions, the processor being connected with the memory through a communication bus, wherein, when the imaging device is operating, the processor executes or facilitates execution of the executable instructions stored by the memory to cause the imaging device to perform operations, comprising:
   determining a gazed object of an eye;
   determining corresponding sub-areas of an imaging lens group according to the gazed object; and
   determining a scaling parameter of the corresponding sub-areas according to the gazed object,
   wherein the determining the gazed object comprises:
      detecting a position of a focus point of the eye according to an optical parameter corresponding to images presented on the fundus and with a defined clarity determined to be greater than a preset value, wherein the optical parameter is the optical parameter of an optical path between an image collection position and the eye; and
      determining the gazed object according to the position of the focus point of the eye.

\* \* \* \* \*